United States Patent
Bashir et al.

(10) Patent No.: US 9,835,634 B2
(45) Date of Patent: Dec. 5, 2017

(54) COUPLED HETEROGENEOUS DEVICES FOR PH SENSING

(71) Applicants: Rashid Bashir, Champaign, IL (US); Bobby Reddy, Savoy, IL (US); Muhammad A Alam, West Lafayette, IN (US); Pradeep R Nair, Kerali (IN); Jonghyun Go, Seongnam-si (KR)

(72) Inventors: Rashid Bashir, Champaign, IL (US); Bobby Reddy, Savoy, IL (US); Muhammad A Alam, West Lafayette, IN (US); Pradeep R Nair, Kerali (IN); Jonghyun Go, Seongnam-si (KR)

(73) Assignees: The Board of Trustees of the University of Illinois, Urbana, IL (US); Purdue Research Foundation, West Lafayette, IN (US)

( * ) Notice: Subject to any disclaimer, the term of this patent is extended or adjusted under 35 U.S.C. 154(b) by 941 days.

(21) Appl. No.: 14/075,557

(22) Filed: Nov. 8, 2013

(65) Prior Publication Data
US 2014/0139204 A1 May 22, 2014

Related U.S. Application Data

(63) Continuation of application No. PCT/US2013/041649, filed on May 17, 2013.
(Continued)

(51) Int. Cl.
*G01R 19/00* (2006.01)
*G01N 33/84* (2006.01)
(Continued)

(52) U.S. Cl.
CPC .............. *G01N 33/84* (2013.01); *C12Q 1/25* (2013.01); *G01N 27/414* (2013.01);
(Continued)

(58) Field of Classification Search
CPC .... G01N 33/84; G01N 27/414; G01N 33/573; G01N 33/5091; G01N 33/5438;
(Continued)

(56) References Cited

U.S. PATENT DOCUMENTS

| 2,058,761 A | 10/1936 | Beckman |
| 5,814,280 A * | 9/1998 | Tomita ............... G01N 27/4148 422/82.01 |

(Continued)

FOREIGN PATENT DOCUMENTS

| WO | WO 2010/037085 | 4/2010 |
| WO | WO 2011/163058 | 12/2011 |

(Continued)

OTHER PUBLICATIONS

Al-Hilli et al. (2006) "Zinc oxide nanorod for intracellular pH sensing," *Applied Physics Letters.* 89:173119.
(Continued)

*Primary Examiner* — Billy Lactaoen
(74) *Attorney, Agent, or Firm* — Lathrop Gage LLP

(57) ABSTRACT

Provided herein are methods and devices for measuring pH and for amplifying a pH signal to obtain ultrasensitive detection of changes in pH. This is achieved by providing a sensor and a transducer, wherein the sensor transconductance is sensitive to changes in pH and the transducer transconductance is not affected by pH change. The transducer instead compensates for changes in the sensor transconductance arising from pH change. The unique configuration of the sensor and transducer with respect to each other provides substantial increases in a pH amplification factor, thereby providing pH sensing devices with a giant Nernst response and, therefore, effectively increased pH sensitivity.

15 Claims, 10 Drawing Sheets

Related U.S. Application Data

(60) Provisional application No. 61/648,261, filed on May 17, 2012, provisional application No. 61/724,368, filed on Nov. 9, 2012.

(51) Int. Cl.

| | | |
|---|---|---|
| *C12Q 1/25* | (2006.01) | |
| *G01N 33/50* | (2006.01) | |
| *G01N 33/543* | (2006.01) | |
| *G01N 33/573* | (2006.01) | |
| *G01N 33/574* | (2006.01) | |
| *G01N 33/94* | (2006.01) | |
| *G01N 27/414* | (2006.01) | |

(52) U.S. Cl.
CPC ..... *G01N 33/5091* (2013.01); *G01N 33/5438* (2013.01); *G01N 33/573* (2013.01); *G01N 33/574* (2013.01); *G01N 33/94* (2013.01); *G01N 2800/709* (2013.01)

(58) Field of Classification Search
CPC .............. G01N 33/94; G01N 33/574; G01N 2800/709; C12Q 1/25
USPC ...................................................... 324/123 R
See application file for complete search history.

(56) References Cited

U.S. PATENT DOCUMENTS

| | | | | |
|---|---|---|---|---|
| 6,740,911 | B1* | 5/2004 | Chou | G01N 27/414 257/252 |
| 9,488,614 | B2* | 11/2016 | Fischer | G01N 27/4145 |
| 2007/0235760 | A1* | 10/2007 | Shim | H01L 29/78 257/192 |
| 2008/0280776 | A1 | 11/2008 | Bashir et al. | |
| 2011/0086352 | A1 | 4/2011 | Bashir et al. | |
| 2011/0315962 | A1 | 12/2011 | Lieber et al. | |
| 2015/0160323 | A1* | 6/2015 | Wen | G01N 27/4145 702/107 |

FOREIGN PATENT DOCUMENTS

| WO | WO 2012/078340 | 6/2012 |
|---|---|---|
| WO | WO 2013/016486 | 1/2013 |

OTHER PUBLICATIONS

American Cancer Society (2011) "Cancer facts and figures," *American Cancer Society*. Atlanta, Georgia.
Barnas et al. (1990) "Novel Magnetoresistance Effect in Layered Magnetic-Structures—Theory and Experiment," *Physical Review B*. 42(13):8110-8120.
Barrett et al. (2004) "Comparative genomic hybridization using oligonucleotide microarrays and total genomic DNA," *Proc. Natl. Acad. Sci. USA*. 101:17765-17770.
Bashir (2004) "BioMEMS: state-of-the-art in detection, opportunities and prospects," *Advanced Drug Delivery Reviews*. 56(11):1565-1586.
Baumann et al. (1999) "Microelectronic sensor system for microphysiological application on living cells," *Sensor. Actuat. B-Chem*. 55(1):77-89.
Benjaminsen et al. (Jun. 27, 2011) "Evaluating nanoparticle sensor design for intracellular pH measurements," *ACS Nano*. 5(7):5864-5873.
Bergveld (1970) "Development of an ion-sensitive solid-state device for neurophysiological measurements," *IEEE Trans. Biomed. Eng*. 17(1):70-71.
Bergveld (1981) "The operation of an ISFET as an electronic device," *Sensor. Actuat*. 1(1):17-29.
Bergveld (1991) "A critical-evaluation of direct electrical protein detection methods," *Biosensors and Bioelectronics*. 6(1):55-72.
Bergveld (1991) "Future applications of ISFETS," *Sensor. Actuat. B-Chem*. 4(1-2)125-133.
Bergveld (1996) "The future of biosensors," *Sensor. Actuat. A-Phys*. 56(1-2):65-73.
Bergveld (2003) "Thirty years of ISFETOLOGY: What happened in the past 30 years and what may happen in the next 30 years," *Sens. Actuators B: Chem*. 88:1-20.
Besselink et al. (2003) "Modification of ISFETS with a monolayer of latex beads for specific detection of proteins," *Biosensors and Bioelectronics*. 18(9):1109-1114.
Bohra et al. (2007) "Textured crystallization of ultrathin hafnium oxide films on silicon substrate," *Applied Physics Letters*. 90:161917.
Bousse et al. (1983) "Operation of chemically sensitive field-effect sensors as a function of the insulator-electrolyte interface," IEEE Transactions on Electron Devices. 30:1263-1270.
Bousse et al. (1984) "The role of buried oh sites in the response mechanism of inorganic-gate pH-sensitive ISFETS," *Sensor. Actuat*. 6(1):65-78.
Brase et al. (2010) "Serum microRNAs non-invasive biomarkers for cancer," *Molecular Cancer*. 9:306.
Bunimovich et al. (2006) "Quantitative real-time measurements of DNA hybridization with alkylated nonoxidized silicon nanowires in electrolyte solution," *J. Am. Chem. Soc*. 128(50):16323-16331.
Callegari et al. (2001) "Physical and electrical characterization of hafnium oxide and hafnium silicate sputtered films," *Journal of Applied Physics*. 90(12):6466-6475.
Cattani-Scholz et al. (2008) "Organophosphonate-based PNA-functionalization of silicon nanowires for label-free DNA dectection," *ACS Nano*. 2(8):1653-1660.
Chen et al. (2009) "Top-down fabrication of sub-30 nm monocrystalline silicon nanowires using conventional microfabrication," *ACS Nano*. 3(11):3485-3492.
Chen et al. (2010) "Atomic layer deposited hafnium oxide gate dielectrics for charge-based biosensors," *Electrochem. Solid. St*. 13(3):G29-G32.
Chen et al. (2010) "In situ doped source/drain for performance enhancement of double-gated poly-Si nanowire transistors," *IEEE Trans. Electron Dev*. 57(7):1608-1615.
Chen et al. (Apr. 18, 2011) "$Al_2O_3$/Silicon NanoISFET with Near Ideal Nernstian Response," *Nano Lett*. 11:2334-2341.
Chen et al. (Apr. 27, 2011) "Current instability for silicon nanowire field-effect sensors operating in electrolyte with platinum gate electrodes," *Electrochem. Solid. St*. 14(7):J34-J37.
Choi et al. (2012), "Quantitative studies of long-term stable, top-down fabricated silicon nanowire pH sensors," *Appl. Phys. A: Mater Sci Process*. pp. 1-8.
Chua et al. (2009) "Label-free electrical detection of cardiac biomarker with complementary metal-oxide semiconductor-compatible silicon nanowire sensor arrays," *Anal. Chem*. 81(15):6266-6271.
Cissell et al. (2008) "Bioluminescence-based detection of microRNA, miR21 in breast cancer cells," *Anal. Chem*. 80(7):2319-2325.
Cohen-Karni et al. (2009) "Flexible electrical recording from cells using nanowire transistor arrays," *Proc. Natl. Acad. Sci. USA*. 106(18):7309-7313.
Corless (Dec. 2, 2011) "Personalized cancer diagnostics," *Science*. 334(6060):1217-1218.
Crampton et al. (2005), "Formation of aminosilane-functionalized mica for atomic force microscopy imaging of DNA," *Langmuir*. 21(17):7884-7891.
Credo et al. (Jan. 19, 2012) "Label-free electrical detection of pyrophosphate generated from DNA polymerase reactions on field-effect devices," *Analyst*. 137(6):1351-1362.
Cui et al. (2001), "Nanowire nanosensors for highly sensitive and selective detection of biological and chemical species," *Science*. 293(5533):1289-1292.
Dankerl et al. (2008) "Resolving the controversy on the pH sensitivity of diamond surfaces," *Physica Status Solidi-Rapid Research Letters*. 2(1):L31-33.

(56) References Cited

OTHER PUBLICATIONS

David et al. (1974) "Site-binding model of the electrical double layer at the oxide/water interface," *Journal of the Chemical Society, Faraday Transactions 1: Physical Chemistry in Condensed Phases.* 70:1807-1818.
de Planell-Saguer et al. (May 20, 2011) "Analytical aspects of microRNA in diagnostics: A review," *Analytica Chimica Acta.* 699(2):134-152.
Deen et al. (2006) "Noise considerations in field-effect biosensors," *Journal of Applied Physics.* 100:074703.
Dorvel et al. (2010) "Vapor-phase deposition of monofunctional alkoxysilanes for sub-nanometer-level biointerfacing on silicon oxide surfaces," *Adv. Funct. Mater.* 20(1):87-95.
Douketis (2001) "Patient self-monitoring of oral anticoagulant therapy: potential benefits and implications for clinical practice," *Am. J. Cardiovasc. Drugs.* 1:245-251.
Douketis et al. (2001) "Twice daily enoxaparin, but not once daily dalteparin, is associated with elevated anti-factor Xa heparin levels at the time of epidural catheter removal," *Blood.* 98(11):707a.
Dunham et al. (2002) "Characteristic genome rearrangements in experimental evolution of saccharomyces cerevisiae," *Proc. Natl. Acad. Sci. USA.* 99(25):16144-16149.
Ecken et al. (2003), "64-channel extended gate electrode arrays for extracellular signal recording," *Electrochimica Acta.* 48(20-22):3355-3362. 2003.
Eijkel et al. (1997) "An ISFET-based dipstick device for protein detection using the ion-step method," *Biosensors and Bioelectronics.* 12(9-10):991-1001.
Elfstrom et al. (2007) "Surface charge sensitivity of silicon nanowires: Size dependence," *Nano Letters.* 7(9):2608-2612.
Elfstrom et al. (2008) "Biomolecule detection using a silicon nanoribbon: Accumulation mode versus inversion mode," *Nanotechnology.* 19:235201.
Elfstrom et al. (2008) "Silicon nanoribbons for electrical detection of biomolecules," *Nano Letters.* 8(3):945-949.
Elibol et al. (2003) "Integrated nanoscale silicon sensors using top-down fabrication," *Applied Physics Letters.* 83(22):4613-4615.
Elibol et al. (2008) "Nanoscale thickness double-gated field effect silicon sensors for sensitive pH detection in fluid," *Applied Physics Letters.* 92:193904.
Elibol et al. (2009) "Localized heating on silicon field effect transistors: Device fabrication and temperature measurements in fluid," *Lab Chip.* 9(19):2789-2795.
Fan et al. (2006) "Highly parallel genomic assays," *Nat. Rev. Genet.* 7(8):632-644.
Fan et al. (2008) "Integrated barcode chips for rapid, multiplexed analysis of proteins in microliter quantities of blood," *Nat. Biotechnol.* 26(12):1373-1378.
Fang et al. (2007) "Electrical detection of single DNA molecules with silicon nanowire devices," *Biophysical Journal.* 551A.
Freeman et al. (2007) "Analysis of dopamine and tyrosinase activity on ion-sensitive field-effect transistor (ISFET) devices," *Chemistry.* 13(26):7288-7293.
Freeman et al. (2007) "Following a protein kinase activity using a field-effect transistor device," *Chem. Commun.* 33:3450-3452.
Fritz et al. (2002) "Electronic detection of DNA by its intrinsic molecular charge," *Proc. Natl. Acad. Sci. USA.* 99(22):14142-14146.
Gabriely et al. (2011) "Context effect: microRNA-10b in cancer cell proliferation, spread and death," *Autophagy.* 7(11):1384-1386.
Gallagher et al. (2008) "Magnetic resonance imaging of pHHHgg in vivo using hyperpolarized (13)c-labelled bicarbonate," *Nature.* 453(7197):940-943.
Gambino et al. (1998), "Silicides and ohmic contacts," *Mater. Chem. Phys.* 52(2):99-146.
Gao et al. (1994) "Determination of the effective charge of a protein in solution by capillary electrophoresis," *Proc. Natl. Acad. Sci. USA.* 91(25):12027-12030.
Gao et al. (2007) "Silicon nanowire arrays for label-free detection of DNA," *Analytical Chemistry.* 79(9):3291-3297.
Gao et al. (2010) "Subthreshold regime has the optimal sensitivity for nanowire FET biosensors," *Nano Letters.* 10(2):547-552.
Gao et al. (Aug. 11, 2011) "Silicon-nanowire-based CMOS-compatible field-effect transistor nanosensors for ultrasensitive electrical detection of nucleic acids," *Nano Lett.* 11(9):3974-3978.
Gaster et al. (2009) "Matrix-insensitive protein assays push the limits of biosensors in medicine," *Nature Medicine.* 15(11):1327-1332.
Gillies et al. (1994) "31P-MRS measurements of extracellular pH of tumors using 3-aminopropylphosphonate," *Am. J. Physiol.* 267(1):C195-C203.
Gillies et al. (2002) "MRI of the tumor microenvironment," *Journal of Magnetic Resonance Imaging.* 16(4):430-450.
Ginet et al. (May 4, 2011) "CMOS-compatible fabrication of top-gated field-effect transistor silicon nanowire-based biosensors," *J. Micromech. Microeng.* 21(6): 1-7.
Go et al. (Dec. 6-8, 2010) "Beating the Nernst limit of 59mV/pH with double-gated nano-scale field-effect transistors and its applications to ultra-sensitive DNA biosensors," In; Electron Devices Meeting (IEDM), 2010 IEEE International (2010). San Francisco, California. pp. 8.7.1-8.7.4.
Go et al. (Jun. 13, 2012) "Coupled Heterogeneous Nanowire—Nanoplate Planar Transistor Sensors for Giant (>10 V/pH) Nernst Response," *ACS Nano.* 6:5972-5979.
Goda et al. (2010) "Detection of microenvironmental changes induced by protein adsorption onto self-assembled monolayers using an extended gate-field effect transistor," *Analytical Chemistry.* 82(5):1803-1810.
Goncharova et al. (2011), "Diffusion and interface growth in hafnium oxide and silicate ultrathin films on Si(001)," *Phys. Rev. B.* 83:115329.
Gresham et al. (2008) "Comparing whole genomes using DNA microarrays," *Nature Reviews Genetics.* 9(4):291-302.
Griffiths (1991) "Are cancer-cells acidic," *British Journal of Cancer.* 64(3):425-427.
Guerra et al. (2009) "Extended gate field effect transistor using $V_2O_5$ xerogel sensing membrane by sol-gel method," *Solid State Sciences.* 11(2):456-460.
Hahm et al. (2004) "Direct ultrasensitive electrical detection of DNA and DNA sequence variations using nanowire nanosensors," *Nano Lett.* 4(1):51-54.
Harvey (1999) "Point-of-care laboratory testing in critical care," *Am. J. Crit. Care.* 8(2):72-83.
Hausmann et al. (2002) "Atomic layer deposition of hafnium and zirconium oxides using metal amide precursors," *Chemistry of Materials.* 14(10):4350-4358.
Heller et al. (2008) "Identifying the mechanism of biosensing with carbon nanotube transistors," *Nano Letters.* 8(2):591-595.
Heneghan et al. (2010) "Circulating microRNAs as novel minimally invasive biomarkers for breast cancer," *Annals of Surgery.* 251(3):499-505.
Henighan (2010) "Manipulation of magnetically labeled and unlabeled cells with mobile magnetic traps," Biophysical Journal 98(3):412-417.
Hou et al. (2006) "Label-free microelectronic PCR quantification," *Analytical Chemistry.* 78(8):2526-2531.
Hou et al. (2007), "Integrated microelectronic device for label-free nucleic acid amplification and detection," *Lab Chip.* 7(3):347-354.
Hsu et al. (2009) "Sodium and potassium sensors based on separated extended gate field effect transistor," *Biomedical Engineering-Applications Basis Communications.* 21(6):441-444.
Iniguez et al. (1999) "A physically-based c-infinity-continuous model for accumulation-mode SOI pMOSFET's," *IEEE Trans. Electron Dev.* 46(12):2295-2303.
International Search Report with Written Opinion corresponding to International Patent Application No. PCT/US2013/41649, dated Oct. 29, 2013.
Ishige et al. (2009) "Extended-gate FET-based enzyme sensor with ferrocenyl- alkanethiol modified gold sensing electrode," *Biosens. Bioelectron.* 24(5):1096-1102.
Iyevleva et al. (2012) "High level of miR-21, miR-10b, and miR-31 expression in bilateral vs. unilateral breast carcinomas," *Breast Cancer Res. Treat.* 131(3):1049-1059.

(56) References Cited

OTHER PUBLICATIONS

Jakobson et al. (1999) "1/f Noise in Ion Selective Field Effect Transistors from Subthreshold to Saturation," *IEEE Transactions on Electron Devices.* 46:259-261.
Jang et al. (1999) "A novel approach for modeling accumulation-mode SOI MOSFETs," *Solid-State Electronics.* 43(1):87-96.
Joachim et al. "Analytical modeling of short-channel behavior of accumulation-mode transistors on silicon-on-insulator substrate," *Jap. J Appl Phys.* 33(1 B):558-562.
Juhasz et al. (2005) "Controlled fabrication of silicon nanowires by electron beam lithography and electrochemical size reduction," *Nano Lett.* 5(2):275-280.
Kallioniemi (2001) "Biochip technologies in cancer research," *Annals of Medicine.* 33(2):142-147.
Kang et al. (2007) "Broad-Wavelength-Range Chemically Tunable Block-Copolymer Photonic Gels," *Nat. Mater.* 6:957-960.
Kilgore et al. (1998) "Evaluating stat testing options in an academic health center: Therapeutic turnaround time and staff satisfaction," *Clin. Chem.* 44(8)1597-1603.
Kilgore et al. (1999) "Cost analysis for decision support: The case of comparing centralized versus distributed methods for blood gas testing," *Journal of Healthcare Management.* 44(3):207-215.
Kim et al. (2004) "An FET-type charge sensor for highly sensitive detection of DNA sequence," *Biosens. Bioelectron.* 20(1):69-74.
Kim et al. (2004) "Field effect transistor-based bimolecular sensor employing a Pt reference electrode for the detection of deoxyribonucleic acid sequence," *Jap. J. Appl. Phys.* 43(6B):3855-3859.
Kim et al. (2006) "An extended gate FET-based biosensor integrated with a si microfluidic channel for detection of protein complexes," *Sens. Actuat. B-Chem.* 117(2):488-494.
Kim et al. (2007) "Ultrasensitive, label-free, and real-time immunodetection using silicon field-effect transistors," *Applied Physics Letters.* 91:103901.
Kim et al. (2009) "Chemosensors for pyrophosphate," *Accounts of Chemical Research.* 42(1):23-31.
Kim et al. (Feb. 20-23, 2011) "pH sensing and noise characteristics of Si nanowire ion-sensitive field effect transistors," In; 2011 IEEE International Conference on Nano/Micro Engineered and Molecular Systems (NEMS). Kaohsiung City, Taiwan. pp. 1233-1236.
Kimura et al. (1990) "FET biosensors," *J. Biotechnol.* 15:(3)239-254.
Knopfmacher et al. (2010) "Nernst Limit in Dual-Gated Si-Nanowire FET Sensors," *Nano Lett.* 10:2268-2274.
Kodadek (2001) "Protein microarrays: Prospects and problems," *Chem. Biol.* 8(2):105-115.
Kokawa et al. (2006) "Liquid-phase sensors using open-gate AlGaN/GaN high electron mobility transistor structure," *J. Vac. Sci. Technol.* B. 24:1972-1976.
Kost (1995) "Point-of-care testing—clinical immediacy, significance, and outcomes," *American Journal of Clinical Pathology.* 104(4):S1.
Kost et al. (1999) "The laboratory-clinical interface: point-of-care testing," *Chest.* 115(4):1140-1154.
Kruise et al. (1992) "Detection of charged proteins by means of impedance measurements," *Sens. Actuat. B-Chem.* 6(1-3):101-105.
Kruise et al. (1997) "Detection of protein concentrations using a pH-step titration method," *Sens. Actuat. B-Chem.* 44(1-3):297-303.
Kukli et al. (2002) "Atomic layer deposition of hafnium dioxide films from hafnium tetrakis(ethylmethylamide) and water," *Chemical Vapor Deposition.* 8(5):199-204.
Lai et al. "pH sensitivity improvement on 8 nm thick hafnium oxide by post deposition annealing," *Electrochemical and Solid-State Letters.* 9(3):G90-G92.
Lambacher et al. (1996) "Fluorescence interference-contrast microscopy on oxidized silicon using a monomolecular dye layer," *Appl. Phys. A-Mater. Sci. Process.* 63(3):207-216.
Lee et al. (2009) "Ion-sensitive field-effect transistor for biological sensing," *Sensors.* 9(9):7111-7131.
Lequin (2005) "Enzyme Immunoassay (EIA)/Enzyme-Linked Immunosorbent Assay (ELISA)," *Clin. Chem.* 51(12):2415-2418.
Li et al. (2004) "Sequence-specific label-free DNA sensors based on silicon nanowires," *Nano Lett.* 4(2):245-247.
Li et al. (2010) "CMOS open-gate ion-sensitive field-effect transistors for ultrasensitive dopamine detection," *IEEE Trans. Electron Dev.* 57(10):2761-2767.
Liang et al. (2007) "Characterization of microRNA expression profiles in normal human tissues," *BMC Genomics.* 8:166.
Liu et al. (Jun. 20, 2011) "Surface immobilizable chelator for label-free electrical detection of pyrophosphate," *Chem. Commun.* 47(29):8310-8312.
Lu et al. (2005) "MicroRNA expression profiles classify human cancers," *Nature.* 435(7043):834-838.
Lucito et al. (1998) "Genetic analysis using genomic representations," *Proc. Natl. Acad. Sci. USA.* 95(8):4487-4492.
Lud et al. (2006) "Field effect of screened charges: Electrical detection of peptides and proteins by a thin-film resistor," *Chemphyschem.* 7(2):379-384.
Luo et al. (2009) "Silicon nanowire sensors for $Hg^{2+}$ and $Cd^{2+}$ ions," *Appl. Phys. Lett.* 94:193101.
Luzinov et al. (2000) "Epoxy-terminated self-assembled monolayers: Molecular glues for polymer layers," *Langmuir.* 16(2):504-516.
Ma et al. (2007) "Tumour invasion and metastasis initiated by microRNA-10b in breast cancer," *Nature.* 449(7163):682-688.
Ma et al. (2010) "Therapeutic silencing of miR-10b inhibits metastasis in a mouse mammary tumor model," *Nature Biotechnology.* 28(4):341-347.
McCarty et al. (2010) "Manipulating tumor acidification as a cancer treatment strategy," *Alternative Medicine Review.* 15(3):264-272.
Milovic et al. (2006) "Monitoring of heparin and its low-molecular-weight analogs by silicon field effect," *Proc. Natl. Acad. Sci. USA.* 103(36):13374-13379.
Misra et al. (1990) "Electrical damage to silicon devices due to reactive ion etching," *Semiconductor Science and Technology.* 5(3):229-236.
Muller et al. (1999) "The electronic structure at the atomic scale of ultrathin gate oxides," *Nature.* 399(6738):758-761.
Nair et al. (2006) "Performance limits of nanobiosensors," *Appl. Phys. Lett.* 88:233120.
Nair et al. (2007) "Dimensionally frustrated diffusion towards fractal adsorbers," *Physical Review Letters.* 99:256101.
Nair et al. (2008) "Screening-limited response of nanobiosensors," *Nano Letters.* 8(5):1281-1285.
Nakamura et al. (2003) "Current research activity in biosensors," *Analytical and Bioanalytical Chemistry.* 377(3):446-468.
Neff et al. (2006) "Electrical detection of self-assembled polyelectrolyte multilayers by a thin film resistor," *Macromolecules.* 39(2):463-466.
Neff et al. (2006) "Silicon-on-insulator based thin film resistors for quantitative biosensing applications," *Phys. Status Solidi A.* 203(14):3417-3423.
Nikolaides et al. (2004) "Characterization of a silicon-on-insulator based thin film resistor in electrolyte solutions for sensor applications," *J. Appl. Phys.* 95:3811-3815.
Ojugo et al. (1999) "Measurement of the extracellular pH of solid tumours in mice by magnetic resonance spectroscopy: a comparison of exogenous F-19 and P-31 probes," *NMR in Biomedicine.* 12(8):495-504.
Olthuis et al. (1994) "Characterization of proteins by means of their buffer capacity, measured with an ISFET-based coulometric sensor-actuator system," *Biosensors and Bioelectronics.* 9(9-10):743-751.
Olthuis et al. (1998) "The exploitation of ISFETS to determine the acid-base behaviour of proteins," *Electrochimica Acta.* 43(23):3483-3488.
Patolsky et al. (2004) "Electrical detection of single viruses," *Proc. Natl. Acad. Sci. USA.* 101(39):14017-14022.
Patolsky et al. (2006) "Detection, stimulation, and inhibition of neuronal signals with high-density nanowire transistor arrays," *Science.* 313(5790):1100-1104.
Patolsky et al. (2006) "Fabrication of silicon nanowire devices for ultrasensitive, label-free, real-time detection of biological and chemical species," *Nature Protocols.* 1(4):1711-1724.

(56) References Cited

OTHER PUBLICATIONS

Patolsky et al. (2006) "Nanowire-Based Biosensors," *Anal. Chem.* 78:4260-4269.
Poghossian et al. (2005) "Possibilities and limitations of label-free detection of DNA hybridization with field-effect-based devices," *Sens. Actuat. B-Chem.* 111:470-480.
Pollack et al. (1999) "Genome-wide analysis of DNA copy-number changes using cDNA microarrays," *Nature Genetics.* 23(1):41-46.
Price (2001) "Regular review—point of care testing," *Brit. Med. J.* 322:1285-1288.
Prinz (1998) "Magnetoelectronics," *Science.* 282:1660-1663.
Raghunand et al. (1999) "Enhancement of chemotherapy by manipulation of tumour pH," *British Journal of Cancer.* 80(7):1005-1011.
Raghunand et al. (1999) "Plasmalemmal ph-gradients in drug-sensitive and drug-resistant mcf-7 human breast carcinoma xenografts measured by p-31 magnetic resonance spectroscopy," *Biochemical Pharmacology.* 57(3):309-312.
Rajan et al. (Jul. 1, 2011) "Optimal signal-to-noise ratio for silicon nanowire biochemical sensors," *Applied Physics Letters.* 98:264107.
Reddy et al. (2011) "High-k dielectric $Al^2O^3$ nanowire and nanoplate field effect sensors for improved pH sensing," *Biomedical Microdevices.* 13(2):335-344.
Reddy, Jr. (May 22, 2012) "Nanoscale BIOFETS for Ultrasensitive pH and Biomolecular Detection," PhD Dissertation, University of Illinois at Urbana-Champaign.
Redon et al. (2006) "Global variation in copy number in the human genome," *Nature.* 444(7118):444-454.
Robertson (2004) "High dielectric constant oxides," *European Physical Journal-Applied Physics.* 28(3):265-291.
Ronaghi et al. (1998) "A sequencing method based on real-time pyrophosphate," *Science.* 281(5375):363.
Rothberg et al. (Jul. 21, 2011) "An integrated semiconductor device enabling non-optical genome sequencing," *Nature.* 475:348-352.
Roychowdhury et al. (Nov. 30, 2011) "Personalized oncology through integrative high-throughput sequencing: A pilot study," *Sci. Transl. Med.* 3(111).
Rudenja et al. (2010) "Low-temperature deposition of stoichiometric $HfO_2$ on silicon: Analysis and quantification of the $HfO_2$/Si interface from electrical and XPS measurements," *Applied Surface Science.* 257(1):17-21.
Sandifer et al. (1999) "A review of biosensor and industrial applications of pH-ISFETs and an evaluation of Honeywell's 'duraFET,'" *Mikrochim. Acta.* 131:91-98.
Saprigin et al. (2005) "Spectroscopic quantification of covalently immobilized oligonucleotides," *Surface and Interface Analysis.* 37(1):24-32.
Schasfoort et al. (1989) "Modulation of the ISFET response by an immunological reaction," *Sens. Actuat.* 17(3-4):531-535.
Schöning et al. (2006) "Bio FEDs (field-effect devices): State-of-the-art and new directions," *Electroanalysis.* 18(19-20):1893-1900.
Sharma et al. (2006) "Silicon-on-Insulator Microfluidic Device With Monolithic Sensor Integration for muTAS Applications," *J. Microelectromech. S.* 15(2):308-313.
Soper et al. (2006) "Point-of-care biosensor systems for cancer diagnostics/prognostics," *Biosens. & Bioelectron.* 21(10):1932-1942.
Spijkman et al. (2010) "Dual-Gate Organic Field-Effect Transistors as Potentiometric Sensors in Aqueous Solution," *Adv. Funct. Mater.* 20:898-905.
Spijkman et al. (Jan. 24, 2011) "Beyond the Nernst-limit with dual-gate ZnO ion-sensitive field-effect transistors," *Appl. Phys. Lett.* 98:043502.
Squires et al. (2008) "Making it stick: convection, reaction and diffusion in surface-based biosensors," *Nature Biotechnology.* 26(4):417-426.
Star et al. (2003) "Electronic Detection of Specific Protein Binding Using Nanotube FET Devices," *Nano Lett.* 3:459-463.

Steinhoff et al. (2003) "pH response of GaN surfaces and its application for pH-sensitive field-effect transistors," *Appl. Phys. Lett.* 83:177.
Stern et al. (2007) "Importance of the Debye screening length on nanowire field effect transistor sensors," *Nano Lett.* 7(11):3405-3409.
Stern et al. (2007) "Label-free immunodetection with CMOS-compatible semiconducting nanowires," *Nature.* 445:519-522.
Stern et al. (2008) "Label-free electronic detection of the antigen-specific t-cell immune response," *Nano Lett.* 8(10):3310-3314.
Stern et al. (2010) "A nanoelectronic enzyme-linked immunosorbent assay for detection of proteins in physiological solutions," *Small.* 6(2):232-238.
Stern et al. (2010) "Label-free biomarker detection from whole blood," *Nature Nanotechnology.* 5(2):138-142.
Stubbs et al. (1995) "Tumor metabolism—the lessons of magnetic-resonance spectroscopy," *Advances in Enzyme Regulation.* 35(35):101-115.
Stuwe et al. (2007), "pH dependence of melanoma cell migration: protons extruded by nhe1 dominate protons of the bulk solution," *J. Physiol.—London.* 585(2):351-360.
Sun et al. (2008) "Effect of fluorescently labeling protein probes on kinetics of protein-ligand reactions," *Langmuir.* 24(23):13399-13405.
Tong et al. (2009) "Novel top-down wafer-scale fabrication of single crystal silicon nanowires," *Nano Lett.* 9(3):1015-1022.
van der Schoot et al. (1987) "The pH-static enzyme sensor—An ISFET-based enzyme sensor, insensitive to the buffer capacity of the sample," *Anal. Chim. Acta.* 199:157-160.
van der Wal et al. (2004) "High-k dielectrics for use as ISFET gate oxides," In; Sensors, 2004. Proceedings of IEEE. 2:677-680.
van Hal et al. (1995) "A novel description of ISFET sensitivity with the buffer capacity and double-layer capacitance as key parameters," *Sens. Actuat. B-Chem.* 24:201-205.
van Hal et al. (1996) "A general model to describe the electrostatic potential at electrolyte oxide interfaces," *Adv. Colloid Interfac.* 69:31-62.
Venkatesan et al. (2009) "Highly sensitive, mechanically stable nanopore sensors for DNA analysis," *Adv. Mater.* 21(27):2771-2776.
Vu et al. (2010) "Fabrication and application of silicon nanowire transistor arrays for biomolecular detection," *Sens. Actuators B: Chem.* 144:354-360.
Wang (2006) "Electrochemical biosensors: Towards point-of-care cancer diagnostics," *Biosens. Bioelectron.* 21(10):1887-1892.
Wang et al. (2005) "Label-free detection of small-molecule-protein interactions by using nanowire nanosensors," *Proc. Natl. Acad. Sci. USA.* 102(9):3208-3212.
Webb et al. (1999) "Mathematical modelling of tumour acidity: Regulation of intracellular pH," *Journal of Theoretical Biology.* 196(2):237-250.
Webb et al. (Aug. 11, 2011) "Dysregulated pH: A perfect storm for cancer progression," *Nature Reviews Cancer.* 11:671-677.
Weir et al. (2007) "Characterizing the cancer genome in lung adenocarcinoma," *Nature.* 450(7171):893.
Wilk et al. (2000) "Hafnium and zirconium silicates for advanced gate dielectrics," *Journal of Applied Physics.* 87(1):484-492.
Yang et al. (2002) "Controlling the threshold voltage of a metal-oxide-semiconductor field effect transistor by molecular protonation of the Si: $SiO_2$ interface," *J. Vac. Sci. Technol. B.* 20(4):1706-1709.
Yang et al. (2006) "A microfluidic device for continuous, real time blood plasma separation," *Lab Chip.* 6(7):871-880.
Yuqing et al. (2003) "Ion sensitive field effect transducer-based biosensors," *Biotechnology Advances.* 21(6):527-534.
Zemel (1990) "Microfabricated nonoptical chemical sensors," *Review of Scientific Instruments.* 61(6):1579-1606.
Zhang et al. (2008) "DNA sensing by silicon nanowire: Charge layer distance dependence," *Nano Lett.* 8(4):1066-1070.

* cited by examiner

COUPLED HETEROGENEOUS DEVICES FOR PH SENSING

CROSS-REFERENCE TO RELATED APPLICATIONS

This application is a continuation of International Application No. PCT/US13/41649 filed May 17, 2013, which claims the benefit of and priority to U.S. Provisional Application No. 61/648,261 filed May 17, 2012. This application also claims the benefit of and priority to U.S. Provisional Application No. 61/724,368, filed Nov. 9, 2012. Each of the above applications are hereby incorporated by reference in their entireties.

STATEMENT REGARDING FEDERALLY SPONSORED RESEARCH OR DEVELOPMENT

This invention was made with government support under RO1-CA20003 awarded by the National Institutes of Health. The government has certain rights in the invention.

BACKGROUND OF INVENTION

The devices and methods disclosed herein are for use in pH measuring and monitoring applications. There is a need in the art for ultrasensitive detection of pH in a rapid and reliable manner. Conventional pH sensors are generally confined by the Nernstian limit of 59 mV/pH, and have a detection limit practically constrained by signal-to-noise interference. Provided herein are devices and methods that vastly improve the pH detection limit by effectively increasing the Nernstian limit by an amplification factor. In this manner, a pH sensitivity that is better than 0.02 pH units is achieved, including as good as 0.002 pH units. Such an improvement represents about an order of magnitude improvement over commercial pH sensors.

SUMMARY OF THE INVENTION

Provided herein are methods and devices that have improved pH sensitivity and ultrasensitive pH detection. This improvement is by specially selecting geometrical and/or electrical properties of two components of the device: a sensor and a transducer, so as to obtain an amplification factor that functions to provide an extrinsic pH sensor response that is increased dramatically beyond the Nernst limit, including by factors of 10, 20, 100 or more, or a range of between about 10 and 1000.

In an aspect, the invention is a method of amplifying a pH signal, such as by providing a sensor comprising a source electrode, a drain electrode, a sensor channel provided between the source and drain electrodes, and a sensing surface over at least a portion of the sensor channel, wherein the sensor channel has a first transconductance. A transducer is provided comprising a source electrode, a drain electrode, and a transducer channel provided between the source and drain electrodes, wherein the transducer channel has a second transconductance, and the second transconductance is greater than the first transconductance. A material is applied to the sensing surface, wherein a change in pH of the material generates a conductance modulation of the sensor channel. A bias of the transducer is adjusted to counterbalance the conductance modulation of the sensor channel, thereby amplifying the pH signal of the material.

In an aspect, the amplifying corresponds to selecting an amplification factor that is defined by:

$$\left(\frac{\mu_1}{\mu_2}\frac{(W/L)_1}{(W/L)_2}\frac{V_{DS,1}}{V_{DS,2}}\right)\frac{C_{OX,1}}{C_{OX,2}} \quad \text{Eq'n (A)}$$

wherein $\mu$ is the channel mobility, W is the channel width, L is the channel length, $V_{DS}$ is the drain bias, $C_{OX}$ is the gate oxide capacitance, and the subscripts 1 and 2 refer to the sensor and the transducer, respectively. Depending on the application of interest, an appropriate amplification factor is obtained by adjusting one or more of the parameters that define the amplification factor, including a geometry, mobility scaling, oxide thickness, and/or bias. In an aspect, the amplification factor is greater than or equal to 10, greater than or equal to 20, greater than or equal to 100, or selected from a range that is between about 20 and 20,000.

In an aspect, the selecting step comprises selecting a width and/or a length of: the transducer, the sensor, or both, so that $(W/L)_1/(W/L)_2$ is greater than or equal to 20.

In an embodiment, any of the sensor channels provided herein is a nanoplate and any of the transducer channels is a nanowire. Such a configuration provides the ability to greatly vary the ratio of $W_1/W_2$ in the above Eq'n (A) so as to obtain a desired amplification factor. In an aspect, $W_1/W_2$ is greater than or equal to 20 and less than or equal to $1\times10^6$. Alternatively, any of the widths may be described in absolute terms, such as a nanoplate width ($W_1$) that is greater than or equal to 1 μm and less than or equal to 100 μm, and/or a nanowire width ($W_2$) that is greater than or equal to 1 nm and less than or equal to 100 nm. In an aspect, $L_1 \neq L_2$. In an aspect, $L_1 = L_2$. Although the term "nanoplate" has traditionally been used to describe objects with about 100 nm dimensions, here we use the term to describe a transistor, including a channel thereof, that is that is about 100 nm thick with width (W) that may be greater than nano scale, including widths on the order of about 1-20 μm wide, to emphasize its pairing with a NW transistor. Accordingly, the term "nanowire" refers to wires that have cross sections on the order of about 100 nm, such as diameters that are about 10 nm to 200 nm, or more specifically rectangular or square cross-sections that are (10 nm-200 nm)×(10 nm-200 nm), and any subranges thereof. The lengths of the nanoplate and nanowire can be on the order of many microns, such as greater than 1 μm, greater than 10 μm, or selected from a range of between about 1 μm and 100 μm.

In an embodiment, the selecting step comprises mobility scaling so that the sensor channel has a higher mobility than a transducer channel mobility. This selecting embodiment may be achieved by providing a first material for the sensor channel and a second material for the transducer channel, wherein the first material has a higher mobility than the second material. Examples of such sensor/transducer (first material/second material) pairs include, but are not limited to: AlGaN/Si; SiNW/Si; GaN/Si. In an aspect, the mobility scaling comprises providing the sensor as part of an n-channel metal-oxide-semiconductor field-effect transistor (nMOS) and the transducer as part of a p-channel metal-oxide-semiconductor field-effect transistor (pMOS). In any of these embodiments, effecting relative changes in sensor and transducer channel mobility provides a means for adjusting the amplification factor of Eq'n (A).

In another embodiment, the selecting step comprises oxide thickness scaling, such as to obtain a $C_{OX,1}$ that is greater than $C_{OX,2}$ by at least a factor of 20. For example, the scaling may be achieved by a dual oxide process to provide an oxide layer thickness of the sensor that is greater than an oxide layer thickness of the transducer. Alternatively, the oxide thickness scaling may be by providing a sensor channel material having a higher k-dielectric than a transducer channel material k-dielectric. Examples of k-dielectric materials include those discussed in WO 2012/078340, hereby incorporated by reference. Alternatively, the oxide thickness scaling may comprise both the oxide layer thickness selection and the higher k-dielectric selection.

In another embodiment, the selecting step comprises bias scaling so that $V_{DS,1}$ is greater than or equal to $V_{DS,2}$ by a factor of at least 20. This bias scaling is particularly suited for applications where tuning of the device is desired, such as to change the dynamic range or the pH sensitivity as the other methods generally are fixed upon device manufacture. In an aspect, therefore, the bias scaling provides real-time tunability of sensor performance, such as a performance wherein the dynamic range of pH is tuned to cover a pH unit range that is between about 0.01 pH units to about 1 pH unit, or a sensitivity that is tuned to provide about 0.001 pH units sensitivity to about 0.02 pH units sensitivity.

In an aspect, any of the methods and devices provided herein may be described by one or more functional parameters, such as having a Nernst response that is greater than or equal to 0.5 V/pH, or that is greater than or equal to 10 V/pH, or that is between about 0.5 V/pH and 100 V/pH and any subranges thereof. In an aspect, the functional parameter is a dynamic pH range of up to 0.5 pH. In an aspect, the functional parameter is a pH sensitivity selected from a range that is greater than or equal to 0.001 pH units and less than or equal to 0.01 pH units.

In an aspect, the transducer channel is biased to a top gate or to a bottom gate. In an aspect, the sensor channel is biased to a fluid gate that is at least partially immersed in the material, such as a material that is a fluid.

In an aspect, the transducer further comprises a transducer surface and the material is provided on the transducer surface in addition to the sensing surface, wherein the second transconductance is substantially independent or is independent of pH, in contrast to the first transconductance. This may be achieved by coating or surface treating the nanowire with a chemically inert and/or non-interacting surface material so that the surface does not bind protons. Alternatively, the transducer may be positioned outside of a well in which the material is confined, in contrast to the sensor's sensing surface.

The methods and devices provided herein are suitable for use in a range of applications, such as nucleotide sequencing, environmental toxic monitoring, pharmaceutical testing, food testing, cancer monitoring, detection of enzyme activity, or any other application where a change in pH provides information about a process or status.

In an embodiment, the material comprises a fluid, such as an electrically-conductive fluid or an electrolyte. In an aspect, the fluid is a biological material, or a liquid in which a biological material is suspended. In an aspect, the material or fluid is defined by a sample volume that is applied to the device, such as a fluid well in which the sensing surface forms at least part of a surface. In an aspect, the sample volume that is applied to the device is a low volume sample, such as less than 1 mL, less than 1 µL, or selected from a range that is between about 0.1 µL and 10 mL, or any sub-ranges thereof.

In an aspect, the material comprises a biological cell and intracellular pH, extracellular pH, or both intracellular and extracellular pH is measured. In an aspect, the biological cell is lysed and the internal pH measured, such as by monitoring a change in pH of a fluid in which the cell is lysed.

Any of the methods and devices provided herein has a sensing surface that comprises an oxide surface, such as an oxide surface that interacts with a proton. For example, the oxide surface may comprise OH surface groups that react with protons to provide a sensor channel transconductance modulation that is pH dependent.

In an embodiment, the invention is a device for measuring changes in pH in a fluid, the device comprising: a sensor comprising a fluid gate, a source electrode, a drain electrode, a sensor channel provided between the source and drain electrodes, and a sensing surface over at least a portion of the sensor channel for receiving the fluid, wherein the sensor channel is a nanoplate in electrical contact with the fluid gate; a transducer comprising a top or a bottom gate, a source electrode, a drain electrode, and a transducer channel provided between the source and drain electrodes, wherein the transducer channel is a nanowire in electrical contact with the top or the bottom gate; wherein the sensor channel has a width ($W_1$) and the nanowire has a width ($W_2$). In one aspect, the ratio of $W_1/W_2$ is greater than or equal to 20, or selected from a range that is greater than or equal to 20 and less than or equal to 1000.

In an aspect, any of the devices have an amplified Nernst response that is greater than or equal to 0.5 V/pH.

In an embodiment, any of the devices have the transducer channel or nanowire is electrically connected to the top gate, having a pH sensitivity that is greater than or equal to 1 V/pH. Alternatively, the transducer channel or nanowire is electrically connected to the bottom gate, having a pH sensitivity that is greater than or equal to 10 V/pH.

In an aspect, the nanoplate has a width to length ratio $(W/L)_1$ and the nanowire has a width to length ratio $(W/L)_2$, wherein $(W/L)_1/(W/L)_2$ is greater than or equal to 20 and less than or equal to 10,000. In an aspect, $L_1 \neq L_2$. The methods and devices provided herein are compatible with a wide range of L, wherein L refers to either or both $L_1$ and $L_2$. In an aspect, $L_1$ and $L_2$ are independently selected to be greater than or equal to 100 nm and less than or equal to 1 mm. In an aspect, $L_1$ and $L_2$ are independently selected to be greater than or equal to 1 µm and less than or equal to 100 µm.

Optionally, the nanoplate and the nanowire comprise Si. Alternatively, the nanoplate and the nanowire comprise materials that are different from each other, such as AlGaN/Si; SiNW/Si; GaN/Si.

In another aspect, the transducer further comprises a transducer surface that contacts the fluid, wherein a transducer channel conductance is not substantially affected by a change in pH of the fluid. In another aspect, the nanowire is physically isolated from the fluid.

Any of the devices provided herein are described in terms of a pH amplification factor, such as an amplification factor that is greater than or equal 20, thereby increasing the Nernst response by at least a factor of 20.

In an aspect, any of the devices described herein are tunable, such as to achieve a user-selected pH sensitivity, a user-selected pH dynamic range, or both a user-selected pH sensitivity and pH dynamic range, including over any of the ranges described herein.

In an aspect, the device has a pH sensitivity that is better than 0.01 pH units.

In an aspect, any of the devices provided herein have a sensor and the transducer with a common source and a common drain. Alternatively, the sensor and transducer are electrically connected to physically distinct sources and physically distinct drains.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

In general, the terms and phrases used herein have their art-recognized meaning, which can be found by reference to standard texts, journal references and contexts known to those skilled in the art. The invention may be further understood by the following non-limiting examples. All references cited herein are hereby incorporated by reference to the extent not inconsistent with the disclosure herewith. Although the description herein contains many specificities, these should not be construed as limiting the scope of the invention but as merely providing illustrations of some of the presently preferred embodiments of the invention. For example, the scope of the invention should be determined by the appended claims and their equivalents, rather than by the examples given.

Example 1

Coupled Heterogeneous Nanowire-Nanoplate Planar Transistor Sensors for Giant Nernst Response Provided herein is a comprehensive theory of pH response of a coupled ISFET sensor to show that the maximum achievable response is given by: $\Delta V/\Delta pH$=59 mV/pH×α, where 59 mV/pH is the Nernst response and α is an amplification factor that depends on the geometrical and electrical properties of the sensor and transducer nodes. While the intrinsic Nernst response of an electrolyte/site-binding interface is fundamental and immutable, we show that by using channels of different materials, areas, and bias conditions, the extrinsic sensor response can be increased dramatically beyond the Nernst limit. We validate the theory by measuring pH response of Si nanowire-nanoplate transistor pair that achieves >10V/pH response and show the potential of the scheme to achieve (asymptotically) the theoretical lower-limit of signal-to-noise ratio (SNR) for a given configuration. Even larger pH response can be obtained based on recent trends in heterogeneous integration on the Si platform.

The search for a miniaturized, highly integrated, and lower cost replacement of the Beckman pH meter[1] dates back to 1970s when Bergveld proposed the CMOS-compatible concept of ion-sensitive field effect transistor[2] (ISFETs, FIG. 1a). Modern variants of ISFETs, based on silicon nanowire (Si-NW)[3] and carbon nanotubes (CNTs)[4], offer novel form factor, prospects of innovative integration, and broader applications, but the sensitivity of all ISFETs are still defined by 59 mV/pH—the Nernst limit associated with an electrolyte and a site-binding surface. Many modern applications of ISFETs, such as the label-free detection of biomolecules in human genome sequencing[5], however, requires the ability to detect just a few hundred protons ($\Delta$pH~0.02) in rapid flux (milliseconds response). For those applications, ability to amplify the Nernst signal can simplify design and increase throughput.

Figure 1:
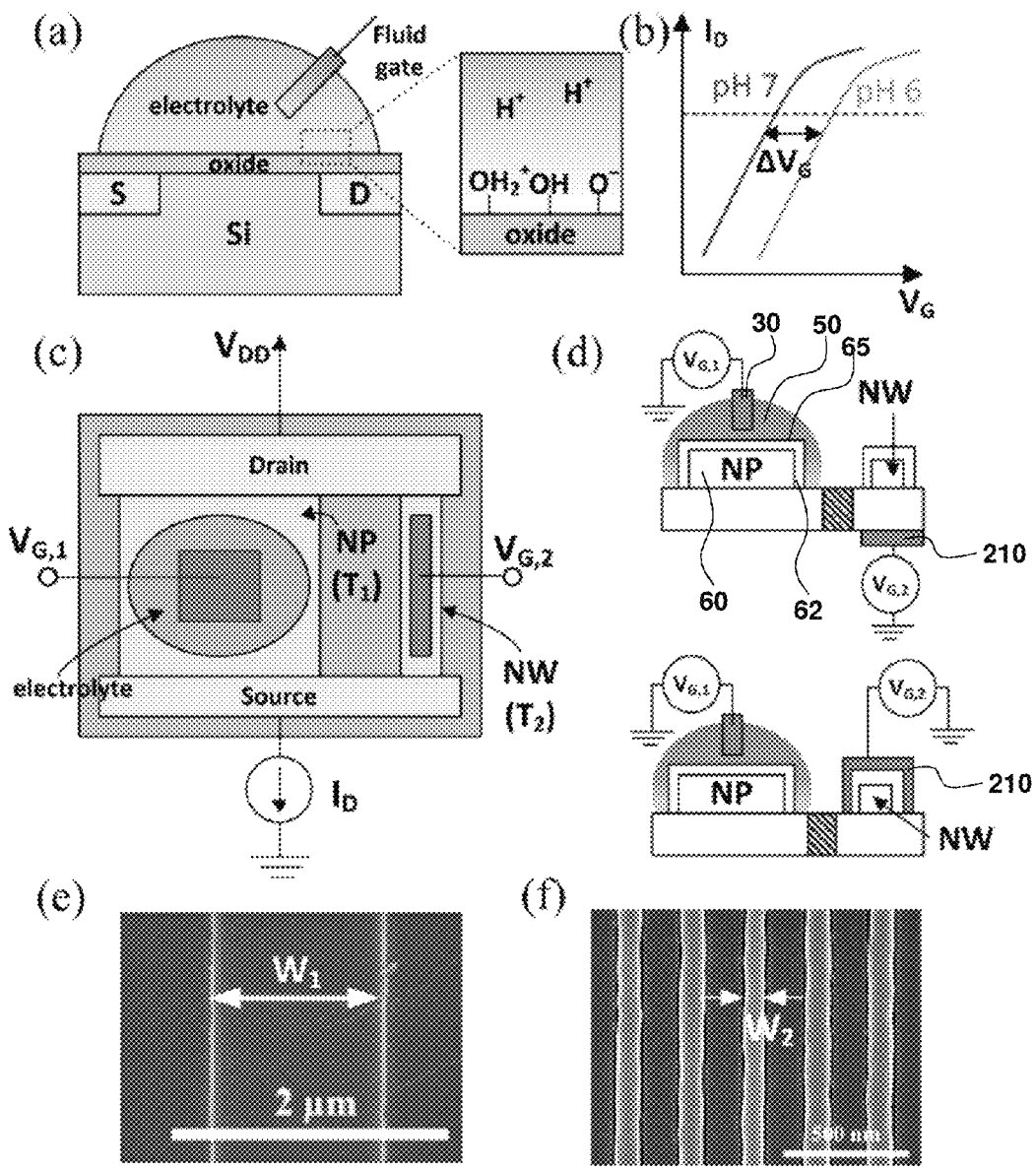
FIG. 1. (a) Schematic diagram of a standard ISFET pH sensor. The surface groups (OH) react with protons ($H^+$) in electrolyte, and the reaction products ($OH_2^+$ and $O^-$) create a net surface charge. (b) Changes in the pH of the electrolyte are reflected in the change of surface charge and eventually changes in channel current ($I_D$) from source (S) to drain (D). The change in fluidgate bias ($\Delta V_G$) required to restore $I_D$ to the original value defines the pH sensitivity of the ISFET. (c) Top view of a coupled nanoplate (NP)-nanowire (NW) pH sensor. NP is always biased by the fluid gate, but the NW can be biased via the top or bottom gate, illustrated as schematics in (d). (e, f) SEM images of a nanoplate (top view) and five nanowires (top view). Only one of the NWs is used as $T_2$ for the sensor scheme proposed.

A recent trend for such amplification is based on double-gate silicon-on-insulator FET (DGFET) and a "super" Nernst response of ~1V/pH has been demonstrated[6-9]. As discussed below, the need to use high fluid gate bias, the poorer quality of bottom oxide, the high cost of silicon-on-insulator (SOI) wafer suggest opportunities to develop alternative techniques. In this example, an alternative is presented based on a highly integrated Si nanoplate (NP)-nanowire (NW) transistor pair that is compatible with planar Si processing technology, see FIG. 1c. In this configuration, the nanoplate acts as the pH sensor node biased through the fluid gate, while the transducer node, defined by the NW, is biased either through the top-gate (top-gated NW) or the bottom gate (bottom-gated NW), as shown in FIG. 1d. The configuration obviates the need for high fluid bias for the NP pH-sensor node, and yet achieves amplified Nernst response ~1V/pH with top-gated NW and (even superior)>10V/pH with bottom-gated NW. Even higher pH response is possible with transistors of different materials integrated onto a common substrate (in FIG. 1, both NW and NP are made of Si). The maximum sensitivity achievable by the scheme is defined by the fundamental trade-off between dynamic range and sensitivity, and practical requirements of the transistor technology.

Operation of Single and Double-Gated ISFETs. A classical ISFET pH sensor involves a simple modification of the standard metal oxide field effect transistor (MOSFET) with the poly-Si gate (on top of the gate oxide) replaced by an electrolyte and a fluid gate, as shown in FIG. 1a. Instead of using poly-Si gate to control the channel current in Si, in ISFET fluid gate affects the source (S) to drain (D) channel current $I_D$ via electrolyte. Any shift in pH of the electrolyte changes the surface charge at the electrolyte-oxide interface through the site-binding process. As shown in FIG. 1b, that ISFET detects pH shifts in the electrolyte by monitoring changes in Si channel current due to charge modulation of surface group at electrolyte-oxide interface[10]. The pH sensitivity is obtained by measuring shift of fluid gate voltage ($\Delta V_G$) at a given amount of pH changes in constant current operation.

The pH sensitivity of an ISFET is understood as follows (see Ref. [10] for detailed analysis): The amphoteric OH groups at gate oxide/buffer undergo protonation/deprotonation of interface as a function of surface proton density, $[H^+]_S$ Assuming Boltzmann distribution for ions in buffer solution, we have $$[H^+]_S = [H^+]_B e^{-q(\psi_0 - V_G)/k_B T} = e^{-2.303 pH - q(\psi_0 - V_G)/k_B T}, \quad (1)$$

where $[H^+]_S$ is the bulk proton density, $pH = -\log_{10}[H^+]_S$, and $\psi_0$ is the oxide/buffer interface potential, $k_B$ is the Boltzmann constant, and T is the temperature. Accordingly, any change in buffer pH manifests as an effective change in surface potential (or an effective change in applied bias for constant current operation) as $\Delta V_G \approx 2.303(k_B T/q)\Delta pH$. Hence the maximum pH sensitivity, known as the Nernst limit, is $\Delta V_G/\Delta pH = 59$ mV/pH in room temperature. In practice, the sensitivity is always less than the intrinsic Nernst limit (associated with electrolyte/oxide interface) due to the high electrolyte screening, protonation affinity of sensor surface, and most importantly, finite semiconductor capacitance of an ISFET[10].

Recently many recent experimental[6-8] and theoretical works[9] suggest this response can be 'amplified' through innovative device geometry, and in fact, a super-Nernst sensitivity ~1V/pH can be achieved by using the double-gate SOI structures (DGFET). There are two gates (top and bottom one) in a DGFET sensor. And the key is to restore the change in $I_D$ due to pH change not by the fluid gate (as in ISFET), but rather through the bottom gate. The conductance change at the top surface of the channel (due to pH shift) is compensated by the change in conductance at the bottom surface to maintain constant current operation. The corresponding pH sensitivity of a DGFET sensor is $$\Delta V_G^{DGFET}/\Delta pH = (59 \text{ mV/pH}) \times \left(\frac{C_{tox}}{C_{box}}\right) \times \alpha_{SN}, \quad (2)$$

where $C_{tox}$ and $C_{box}$ are the top and bottom gate oxide capacitance, so that the amplification factor $\alpha = (C_{tox}/C_{box}) \alpha_{SN} >> 1 (\alpha_{SN} \leq 1)$. For DGFET sensors, the bias and geometry dependent factor $\alpha_{SN} < 1$. Note that the intrinsic Nernst limit (59 mV/pH), associated with electrolyte and site-binding layer is fundamental and cannot be changed by new device configurations (ISFET or DGFET) or novel transducers. The amplified extrinsic Nernst response, however, simplifies detection and improves the practical signal-to-noise ratio (SNR), and is utilized herein to obtain high-sensitivity pH sensors.

For maximum sensitivity, $\alpha_{SN} \to 1$, of a DGFET sensor (Eq. 2), the top channel of the device must be biased in inversion through the fluid gate. Biasing the fluid gate at high voltage is challenging because (i) large fluidic bias often leads to significant leakage current and reduced device lifetime[11], and (ii) if the bias exceeds the formal potential of the electrode, a Butler-Volmer reaction[12] at the fluidic electrode may make the fluid gate potential undefined. Moreover, a shared bottom gate electrode of the DGFET technology makes it difficult to integrate multiple, individually accessible sensors within a common platform, as required in applications such as Ref. [5]. Finally, applying too high a bias on the poorer-quality bottom oxide may lead to hysteresis and unstable device operation. Hence, a super-Nernst sensor that does not require high fluid bias, is not constrained by the geometric/material features of the DGFET, and can be integrated better with the traditional planar technology, is desirable.

"Giant" Nernst (GN) scheme. Consider an accumulation-mode NP-NW transistor pair shown in FIG. 1c. Here, the NP FET acts a sensor transistor $T_1$ and is exposed to the buffer solution for pH sensing, while the NW FET $T_2$ acts as a transducer and is isolated from the buffer, or is not reactive to the buffer. Since the transistors are compatible with planar top-down technology and are processed simultaneously, the process is simple and no additional masks are necessary.

For the accumulation-mode devices, the drain current modulation in $T_2$ is given as $$\Delta I_{D,2} = \mu_2 C_{OX,2}(W/L)_2 V_{DS,2} \Delta V_{G,2}, \quad (3)$$

where $\mu_2$ is the channel mobility, $C_{OX,2}$ is the gate oxide capacitance, W and L is the channel width and length, $V_{DS,2}$ is the drain bias, and $\Delta V_{G,2}$ is the gate bias modulation. Since $T_1$ and $T_2$ are in accumulation regime, the band bending at the channel surface is very small. Hence the current modulation of $T_1$ due to any pH-induced modulation of top-oxide/buffer interface potential is given by $\Delta I_{D,1} = \mu_1 C_{OX,1}(W/L)_1 V_{DS,1} \Delta V_{G,1}$ (note that $\Delta V_{G,1}$ is limited by the Nernst limit). The scheme requires adjustment of the bias of $T_2$ to counterbalance the conductance modulation of $T_1$, so that $$\frac{\Delta V_{G,2}}{\Delta V_{G,1}} = \left(\frac{\mu_1}{\mu_2}\frac{(W/L)_1}{(W/L)_2}\frac{V_{DS,1}}{V_{DS,2}}\right)\frac{C_{OX,1}}{C_{OX,2}} = \alpha_{GN}\frac{C_{OX,1}}{C_{OX,2}}. \quad (4)$$

Equation (4) suggests that GN scheme achieves significant amplification over DGFET sensors (i.e., $\alpha_{GN} \gg \alpha_{SN}$) by (i) Scaling of device dimension, so that W/L of $T_1$ far exceeds that of $T_2$ (and hence the use of NP and NW transistor couple). (ii) Mobility scaling so that $T_1$ has higher mobility than $T_2$. This can be achieved by using NMOS/PMOS pair for $T_1/T_2$ or by using different channel materials. (iii) Oxide thickness scaling—this option is similar to the DGFETs. For maximum amplification, $C_{OX,1} \gg C_{OX,2}$. This is achieved through oxide thickness scaling in a dual oxide process or by using higher-k dielectrics for $T_1$ compared to $T_2$ or a combination thereof. And finally, (iv) Bias scaling so that $V_{DS}$ of $T_2$ is smaller than that of $T_1$. This option of bias scaling provides a post-process, point-of-care option to tune the sensor performance. Since the geometry of DGFET precludes the use of device, bias, and mobility scaling, the response is typically limited to ~1V/pH.

Figure 2:
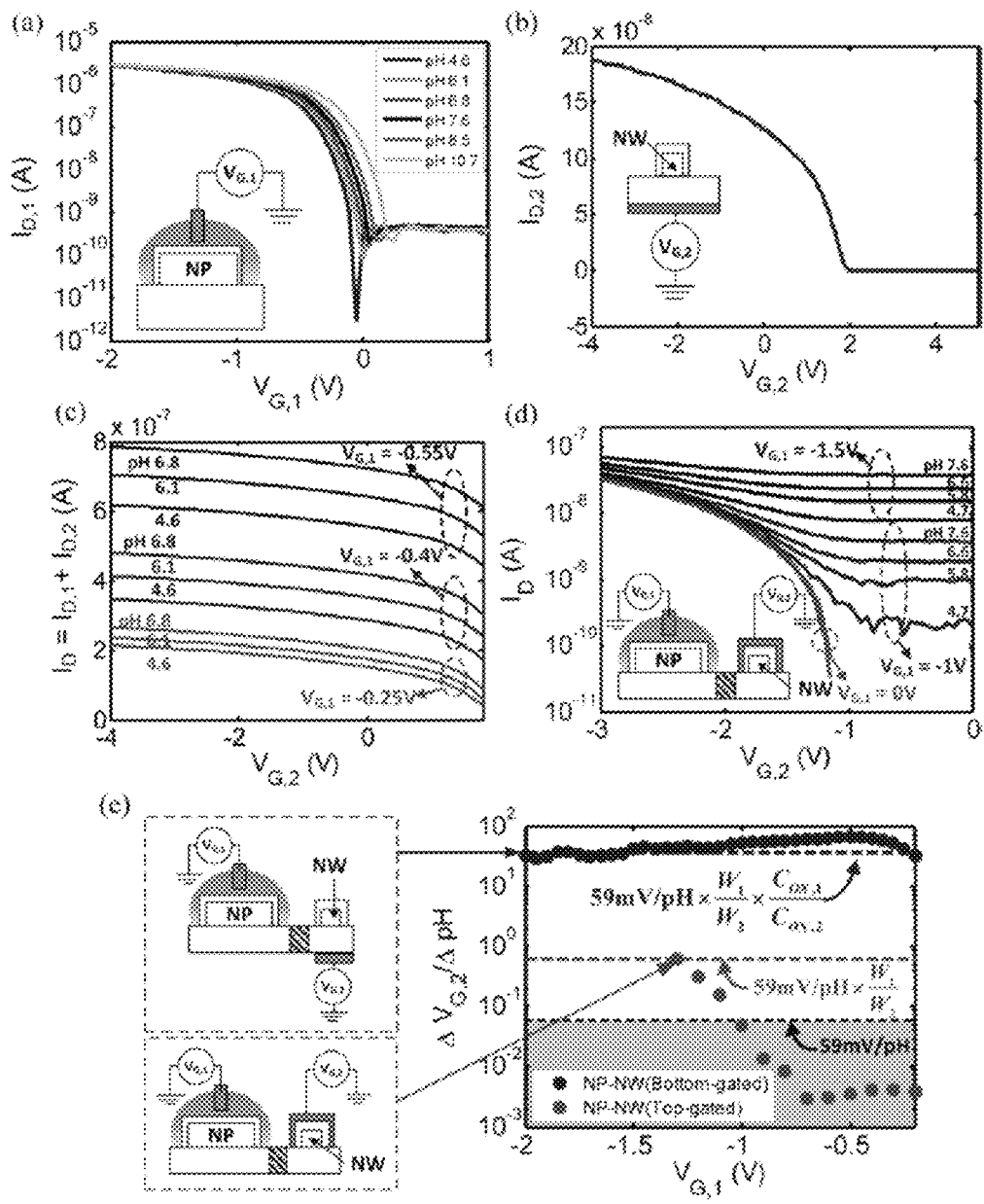
FIG. 2. (a, b) Measured transfer characteristics of a nanoplate (serves as $T_1$) and bottom-gated nanowire ($T_2$), respectively. (c) Transfer characteristics of combined response of (a) and (b)—NP coupled with bottom-gated NP—plotted as a function of $V_{G,2}$. (d) Transfer characteristics of combined currents of a pair of NP and top-gated NW sensor with varying pH and $V_{G,1}$. (e) Measured pH sensitivity (circles) of coupled NP-NW sensors depending on NW bias configurations: bottom gate (top of plot dots, extracted from (c)) and top gate (lower dots, extracted from (d)) sweep. The dashed lines indicate the corresponding theoretical estimates dictated by Eq (4). The solid shaded region represents the classical sensitivity regime below the Nernst limit (59 mV/pH).

FIG. 2 demonstrates the experimental validation of Giant Nernst (GN) scheme, with the maximum GN response of >10V/pH. Let us consider two different biasing configurations for the NW ($T_2$) illustrated in FIG. 1d and compare their performances. In the first configuration, the nanowire $T_2$ is operated through the bottom (BG) gate, and in the second one, through its top gate (TG) (Note $T_1$ is always biased via the fluid gate).

To understand the overall response of first configuration (bottom gate operation of $T_2$) we first characterize the $T_1$-$T_2$ responses independently (FIGS. 2a and 2b). The pH sensitivity of a stand-alone nanoplate ($T_1$) is obtained by the measuring transfer characteristics ($I_{D,1}$ vs. $V_{G,1}$) of a nanowire in solution for various pH values, as shown in FIG. 2a. The responses are stable and repeatable over many hours of operation. We find that stand-alone response of $T_1$ is 46 mV/pH, always below the Nernst limit, as expected. For the GN amplification, $T_1$-$T_2$ coupling is essential, as predicted by Eq. (4). FIG. 2b shows the isolated transfer characteristics ($I_{D,2}$ vs. $V_{G,2}$) of the nanowire ($T_2$) measured in dry air with bottom gate operation.

Recalling the current change in $T_1$ ($\Delta I_{D,1}$) needs to be compensated by $T_2$ ($\Delta I_{D,2} = \Delta I_{D,1}$), we obtain the "combined" transfer characteristics ($I_D$ vs. $V_{G,2}$ shown in FIG. 2c), where the total current ($I_D$) is the sum of individual currents of $T_1$ ($I_{D,1}$) and now top-gated $T_2$ ($I_{D,2}$). FIG. 2c shows combined current vs. the NW gate bias ($V_{G,2}$) with different $V_{G,1}$ and pH. Since the current changes in $T_1$ needs to be compensated by $T_2$ (i.e., $\Delta I_{D,1} + \Delta I_{D,2} = 0$ or $I_D = I_{D,1} + I_{D,2}$ is fixed), the NW gate bias $V_{G,2}$ needs to be shifted versus pH changes ($\Delta$pH) at the constant current level of $I_D$ vs. $V_{G,2}$ in FIG. 2c. For each $V_{G,1}$ we measure the shift of curves ($\Delta V_{G,2}$) for a constant current level. This measured sensitivity ($\Delta V_{G,2}/\Delta$pH) of the first configuration is shown in FIG. 2e as dots at the top of the plot. Since $T_2$ is operated via bottom gate and the channel lengths of $T_1$ and $T_2$ are the same ($L_1 = L_2$), the theoretical estimate of $\alpha_{GN}$ equals to $(W/L)_1/(W/L)_2 \times (C_{OX,1}/C_{OX,2}) = (W_1/W_2) \times (EOT_{OX,2}/EOT_{OX,1}) = (2 \text{ μm}/50 \text{ nm}) \times (145 \text{ nm}/7.3 \text{ nm}) \approx 794$, so the sensitivity is 46 mV/pH×794≈36V/pH, shown as the dashed line in FIG. 2e, which is consistent with our measurement. This NP-NW sensitivity is significantly better than that of DGFET sensors (i.e., $\alpha_{GN} \gg \alpha_{SN}$). This amplification reflects the fact that the current level of $T_1$ (FIG. 2a) is 1-2 orders of magnitude higher than that of $T_2$ (FIG. 2b) since the nanoplate ($T_1$) FET has much higher (W/L) ratio compared to that of the nanowire ($T_2$) FET (i.e., $(W/L)_1 = 40 \times (W/L)_2$ for these particular devices). Note that it is not possible to obtain such high gain from DGFET sensors reported in the literature, because the oxide area, mobility, and drain-bias of the sensor and transducer channels are coupled by common substrate of DGFET, so that $\alpha_{SN} \approx 1$.

To measure the pH sensitivity in the second configuration of NW biasing (top gate operation of $T_2$, sensitivity shown as dots in the middle and bottom of the plot in FIG. 2e) we also measure "combined" transfer characteristics ($I_D$ vs. $V_{G,2}$ shown in FIG. 2d) of a nanoplate and a top-gated nanowire. We follow the same procedure to extract the corresponding pH sensitivity as in the first configuration (with bottom-gated nanowire). FIG. 2e show the pH sensitivity ($\Delta V_{G,2}/\Delta$pH) measured in $T_2$ as a function of NP fluid gate bias ($V_{G,1}$). Since both $T_1$ and $T_2$ are biased via the top gate and have the same top oxide dimension, the sensitivity amplification is achieved by different (W/L) ratios. The effective transistor width of the NW sensor is $W_2^{eff} = W_2 + 2H_2 \approx 3W_2$, because the height of nanowire ($H_2$) is similar to $W_2$ and the gate bias couples to all three surfaces electrostatically. The estimated sensitivity of 46 mV/pH×($W_1/W_2^{eff}$)≈0.613V/pH, shown as dashed lines in the middle of the plot of FIG. 2e, matches well with the experimental data in the accumulation regime. This result implies that the amplification comparable to DGFET can be easily achieved with conventional top-gated MOSFETs with proper design of device geometries. Although the bottom-gated NW (top of plot dots, FIG. 2e) gives higher sensitivity compared to top gated NW configuration (middle to lower plot dots, FIG. 2e) due to its thicker (bottom) oxide, in practice one cannot scale the bottom oxide arbitrarily without introducing excessive defects that leads to device instability and hysteresis. Also, the availability of top contact simplifies interconnection in a massively parallel circuit. Therefore, there may be many practical reasons to prefer the top-gated NW configuration for device application.

Figure 3:
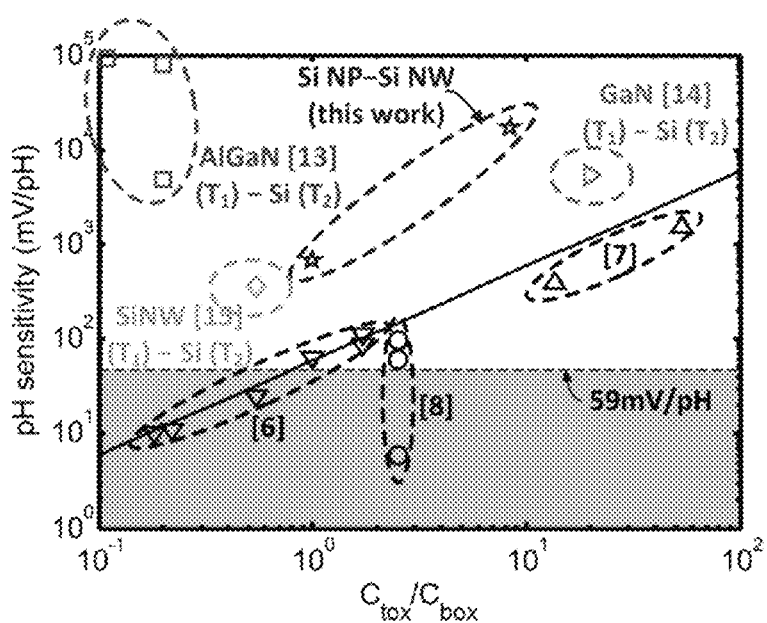
FIG. 3. The simulated pH sensitivity of GN scheme with various types of sensing devices ($T_1$ in FIG. 1c) in the literature: AlGaN[13] (squares), GaN[14] (▷), and SiNW[15] (◇)-based ISFETs. Here a Si n-MOSFET serves as $T_2$. The rest (black) symbols indicate the experimental data from several DGFET sensors in the literature.[6-8] The solid black line represents the theoretical limit of the DGFET sensors.

Eq. (4) suggests that the sensor response could be further improved if the NP and NW sensors are made of different channel materials, so that their mobility asymmetry ($\mu_1/\mu_2 \gg 1$) can be used for the amplified sensor response. To estimate the possible gain in sensitivity by combing transistors of different materials, we first measure the transfer characteristics of a set of Si n-MOSFET devices, which would serve as the transducer node, $T_2$. Next, we extract the slopes of pH responses ($\Delta I_D/\Delta$pH) of devices with different channel materials[13-15] reported in the literature, each of which may potentially serve as the sensor node, $T_1$. Finally, we calculate the combined pH sensitivity of these heterogeneous $T_1$-$T_2$ pairs. FIG. 3 compares the responses so obtained with those from DGFET and ISFETs sensors reported in the literature. As expected, regardless the material characteristics or device dimensions, all the data from the literature based on DGFET and ISFET sensors (black symbols) lie below $\alpha_{SN} \approx 1$ line (the solid black line). In DGFET sensors[6-8], pH response of ~1V/pH is can be achieved. For the proposed GN scheme based on $T_1$-$T_2$ pair, the corresponding pH sensitivity far exceeds DGFET response ($\alpha_{GN} \gg 1$), especially with high-mobility devices (such as GaN, AlGaN) serving as $T_1$, and one can achieve even higher sensitivity (up to 100V/pH regime) by pairing planar FETs with different materials and dimensions into a single sensing entity. Eq. (4) therefore defines the fundamental upper limit of pH sensing for NW-NP based sensors. In practice, this upper limit may not be achieved due to fundamental and practical issues, as discussed in the next section. In an aspect, any of the $T_1/T_2$ pairs provided in FIG. 3, or the literature associated herein, are utilized in any of the methods and devices provided herein to further increase the amplification factor.

Considerations of Dynamic Range, SNR, and minimum pH resolution In contrast to ISFET pH sensor showing wide dynamic range of pH sensing[16], the high sensitivity of the GN scheme is realized at the expense of reduced dynamic range (analogous to the gain-bandwidth product of a traditional transistor). For many applications in healthcare, where the dynamic range of interest is small (7.35-7.45 for human blood pH; $\Delta$pH~0.02 for Ref. Error! Reference source not found.), the tradeoff of higher sensitivity for reduced dynamic range is fully justified. However, excessive gain requires repeated changing of DC bias to cover the pH-range of interest, which is cumbersome and counterproductive. In addition, practical concerns of applying high-bias on gate oxide (for the bottom-gated NW corresponding to top plot dots in FIG. 2e) that may lead to leakage and hysteresis may also limit the maximum gain achievable from a NP-NW sensor combination.

Regarding the signal-to-noise ratio (SNR), another key parameter of pH sensor, it is important to realize that the theoretical lower limit of SNR and minimum pH-resolution ($\Delta$pH$_{min}$) of the GN scheme are still defined by those of its detector ($T_1$). In practice, however, fundamental considerations of measurement noise and biasing configuration ensure that the GN-scheme achieves better $\Delta$pH$_{min}$ far more easily than either NP or NW sensor could in isolation, as discussed below.

The 1/f noise is the dominant source of noise at frequencies relevant for pH sensors[17] and its power-spectrum is given by $S_{V_G} \sim \langle \delta V_G \rangle^2 \propto 1/A$ (A is a device area), or $$\sqrt{\langle \delta V_G \rangle^2} \sim \gamma / \sqrt{A}$$

is a preractor). For a typical single NW pH sensor this noise-floor makes the pH-resolution limited to $$\Delta pH_{min}^{NW} \sim 3\sqrt{\langle \delta V_{G,NW} \rangle^2} \Big/ 0.059 \sim 3\gamma_{NW} \Big/ \left(0.059\sqrt{A_{NW}}\right). \quad (5)$$

Indeed, a key concern for typical NW pH sensor is that such low resolution due to small $A_{NW}$ might be unacceptable for many physiological applications[18].

Figure 4:
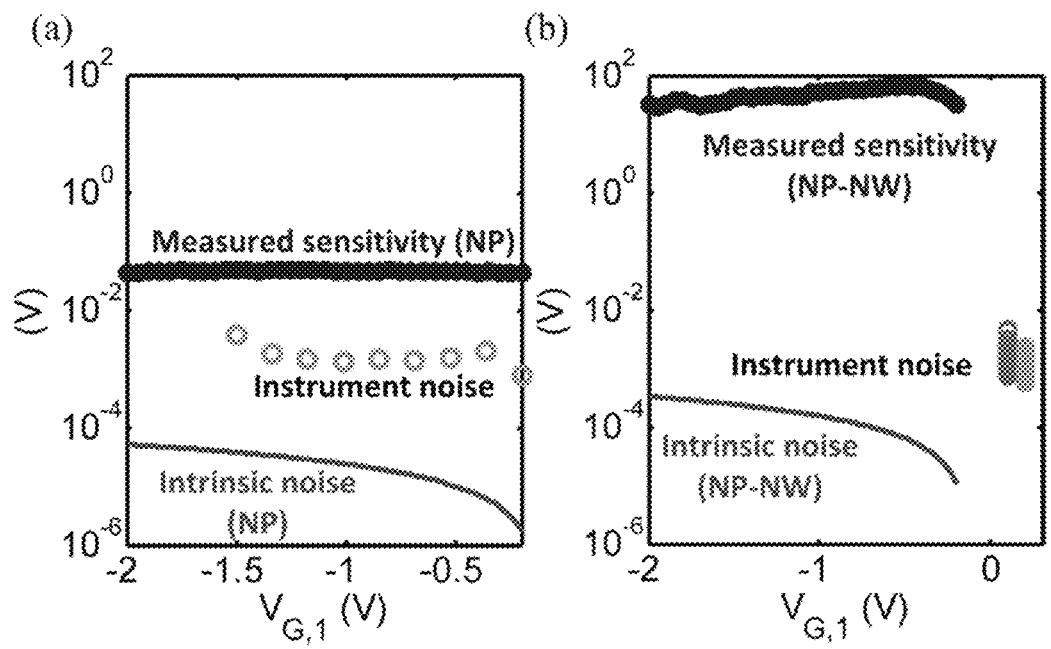
FIG. 4. (a) The measured sensitivity (top of plot dots) of an isolated nanoplate ($T_1$) sensor and instrument noise (open circles) as a function of nanoplate gate bias ($V_{G,1}$), as defined in FIG. 1d. (b) Corresponding plot for the nanoplate-nanowire ($T_1$-$T_2$) sensor scheme proposed in this paper. The measured sensitivity in (b) represents the top of plot dots in FIG. 2e. The theoretical lower limit of 1/f noise are also shown (solid curve).

On the other hand, if the larger area NP sensor ($T_1$) is used in the ISFET configuration, the noise floor (solid line, FIG. 4(a)) and improves the pH resolution considerably, i.e., $$\Delta pH_{min}^{NP} \sim 3\sqrt{\langle \delta V_{G,NP} \rangle^2} \Big/ 0.059 \sim 3\gamma_{NP} \Big/ \left(0.059\sqrt{A_{NP}}\right), \quad (6)$$

as defined by the vertical gap (in log plot) between the top dots and the bottom line in FIG. 4a. For the NP-NW sensor used in the GN scheme, pH sensitivity is amplified (0.059× $\alpha_{GN}$, dots in FIG. 4b) and so is the voltage noise (curve in FIG. 4b). However, its pH resolution is still fundamentally limited by NP ($T_1$) noise because if an instantaneous pH signal unresolved in NP-sensor probe due to noise, it will also remain unresolved in NP-NW combination, thus $\Delta$pH$_{min}^{NP-NW}$=$\Delta$pH$_{min}^{NP}$. Nevertheless, since $A_{NP} \gg A_{NW}$, the pH-resolution is considerably improved compared to single NW sensor: this improvement reflects the reduction in noise-floor due to larger area of NP sensor itself ($T_1$), not due to the NP-NW ($T_1$-$T_2$) combination.

The additional SNR advantage of $T_1$-$T_2$ combination becomes apparent, however, when the noise of the measurement instrument, $\delta V_{Ins}$, is taken into account. If $\delta V_{NP} < \delta V_{Ins}$—as can always be conveniently arranged by increasing the size of the NP ($T_1$) transistor, we find that the pH resolution for the NP alone would have been limited by instrument noise, i.e., $$\Delta pH_{min}^{ins}\Big|_{NP} \sim 3\sqrt{\langle \delta V_{ins} \rangle^2} \Big/ 0.059 \gg \Delta pH_{min}^{NP},$$

and therefore the signal from the NP alone will remain poorly resolved. However, the same signal can still be detected by the $T_1$-$T_2$ combination as $$\Delta pH_{min}^{ins}\Big|_{NP-NW} \sim 3\sqrt{\langle \delta V_{ins} \rangle^2} \Big/ (0.059 \times \alpha_{GN})$$

if $\delta V_{ins}$ is larger than $\delta V_{NW}$ and $\delta V_{NP}$ thus $\Delta pH_{min}^{ins}|_{NP} \gg \Delta pH_{min}^{ins}|_{NP-NW}$ (See Table S1). This is illustrated by the increasing gap between instrument noise (middle band) and sensitivity (top dots) in FIG. 4(a) vs. 4(b), respectively. This is because in the GN scheme the sensitivity is amplified by the area-ratio, while the noise depends on the square-root of the area. Note that this improvement cannot be obtained by simply adding an amplifier following a sensor node, because the SNR ratio remains unchanged in that case.

In this example, we establish a framework of a new class of ISFET-sensors that achieves high sensitivity by physically decoupling the sensor from the transducer node. This principle is used to design a nanoplate-nanowire transistor pair, which shows (consistent with theoretical prediction) sensitivity>10V/pH, which is significantly higher than previous reports based on DGFET pH sensors. Furthermore, we show that pH sensitivity close to 100V/pH may be achieved by incorporating high mobility materials as a sensor node coupled to a low-mobility traducer. The high sensitivity improves pH-resolution as well as signal-to-noise ratio, especially when sensor precision is limited by the noise of the measurement instrument. The improvement of sensitivity, however, must be counter-balanced against the requirement of dynamic range for pH sensing and practical requirements of device scaling. This generic nature of the concept, combined with its compatibility to conventional top-down CMOS processing technology, should make the concept relevant for applications in biomedical areas such as proton-based genome sequencers, environmental toxin monitoring, pharmaceutical testing, etc., in which precise pH monitoring is critical to its sequencing accuracy.

Example 2

Fabrication Methods of Nanowire and Nanoplate Devices

The devices are fabricated using top down fabrication, starting with bonded SOI wafers. 8" bonded SOI wafers (SOITECH) doped p-type at $10^{15}/cm^2$ with BOX thickness of 145 nm and superficial silicon thickness of 55 nm were first laser cut into 4" wafers by Ultrasil Corp. Wafers were then oxidized for 11 minutes at 1000° C. to grow 30 nm of oxide and placed into buffered oxide etch (BOE) to thin down the top silicon to around 350 Å. Wafers were doped with boron at 10 KeV at a dose of $10^{14}$ cm$^{-2}$ and a tilt of 7°. Next, the gate dielectric was formed. For $SiO_2$ devices, the wafers are dry oxidized for 1 minute at 1000° C. to form a gate oxide of around 50 Å, which was measured via ellipsometry on monitor wafers also present during the oxidation run. This also serves as a dopant activation step. For $HfO_2$ devices, after a brief BOE dip and dopant activation in nitrogen for 3 minutes at 1000° C., the wafers were placed into an atomic layer deposition (ALD) machine for 150 cycles of $HfO_2$ for a target thickness of 150 Å. Wafers were then subjected to a Rapid Thermal Anneal (RTA) for 1 min at 950° C., followed by a Forming Gas Anneal (FGA) for 30 minutes at 450° C. in 5% $H_2$ in $N_2$ to reduce interfacial trapped charge, mobile charge, and fixed charge. Next, vias were formed in the silicon mesas with optical lithography and subsequent BOE etch to make solid, crack-free connection between metal interconnects and the silicon layers. AFM was performed over these regions to determine the silicon thickness ($\approx$300 Å) and the gate dielectric thickness ($\approx$50 Å for $SiO_2$, 150 Å for $HfO_2$).

Device Measurement in pH Environment. The pH measurements utilized two separate devices. The main sensing chip with the nanoplate device (2 μm wide) had a 150 Å thick $HfO_2$ dielectric, while the device exhibiting the GN response (a 50 nm wide nanowire device) contained a 50 Å thick $SiO_2$ dielectric. Both chips were fitted with open PDMS wells for containing the fluid. The values for the pH for each solution were measured separately with a commercial pH meter. The fluidic environments over the two separate chips were biased with two leak-free Ag/AgCl reference electrodes purchased from Warner Instruments. A 1× phosphate buffer saline (PBS) solution at pH 7.4 was used for the nanowire device for the entire experiment to enable normal transfer characteristics. Robinson buffers (0.04 M of phosphoric, boric, and acetic acid) with titrated HCl and NaOH, which have good buffering capacity over wide pH ranges, were manually pipetted and rinsed in the PDMS well over the nanoplate device, followed by a 5 minute settling time to allow the surface charge to equilibrate. Transfer characteristics were measured using a Keithley 4200 semiconductor characterization system. The source and drain nodes of the devices were shorted together to create the full GN response sensor, and current was measured at the shorted source nodes of the devices.

References

[1] Arnold O. Beckman, Henry E. Fracker, Apparatus for Testing Acidity, U.S. Pat. No. 2,058,761 (1936).
[2] Piet Bergveld, Sens. Actuators B: Chem. 88, pp. 1-20 (2003).
[3] Fernando Patolsky, Gengfeng Zheng and Charles M. Lieber, Anal. Chem. 78, pp. 4260-4269 (2006).
[4] Alexander Star, Jean-Christophe P. Gabriel, Keith Bradley, and George Grüner, Nano Lett. 3, pp. 459-463 (2003).
[5] Jonathan M. Rothberg, Wolfgang Hinz, Todd M. Rearick, Jonathan Schultz, William Mileski, Mel Davey, John H. Leamon, Kim Johnson, Mark J. Milgrew, Matthew Edwards et al., Nature 475, pp. 348-352 (2011).
[6] Mark-Jan Spijkman, Jakob J. Brondijk, Tom C. T. Geuns, Edsger C. P. Smits, Tobias Cramer, Francesco Zerbetto, Pablo Stoliar, Fabio Biscarini, Paul W. M. Blom, and Dago M. de Leeuw, Adv. Funct. Mater. 20, pp. 898-905 (2010).
[7] M. Spijkman, E. C. P. Smits, J. F. M. Cillessen, F. Biscarini, P. W. M. Blom, and D. M. de Leeuw, Appl. Phys. Lett. 98, 043502 (2011).
[8] O. Knopfmacher, A. Tarasov, Wangyang Fu, M. Wipf, B. Niesen, M. Calame, and C. Schonenberger, Nano Lett. 10, pp. 2268-2274 (2010).
[9] Jonghyun Go, Pradeep R. Nair, Bobby Reddy, Brian Dorvel, Rashid Bashir, and Muhammad A. Alam, Electron Devices Meeting (IEDM), 2010 IEEE International (2010).
[10] Luc Bousse, Nico F. De Rooij, and Piet Bergveld, Electron Devices, IEEE Transactions on, 30, pp. 1263-1270 (1983).
[11] Eric Stern, James F. Klemic, David A. Routenberg, Pauline N. Wyrembak, Daniel B. Turner-Evans, Andrew D. Hamilton, David A. LaVan, Tarek M. Fahmy, and Mark A. Reed, Nature, 445, pp. 519-522 (2007).
[12] A. J. Bard and L. R. Faulkner, Electrochemical Methods: Fundamentals and Applications, John Wiley, New York, 1980.
[13] Takuya Kokawa, Taketomo Sato, Hideki Hasegawa, and Tamotsu Hashizume, J. Vac. Sci. Technol. B 24, pp. 1972-1976 (2006).
[14] G. Steinhoff, M. Hermann, W. J. Schaff, L. F. Eastman, M. Stutzmann, and M. Eickhoff, Appl. Phys. Lett. 83, 177 (2003).
[15] X. T. Vu, R. GhoshMoulick, J. F. Eschermann, R. Stockmann, A. Offenhäusser and S. Ingebrandt, Sens. Actuators B:Chem. 144, pp. 354-360 (2010).
[16] Songyue Chen, Johan G. Bomer, Edwin T. Carlen, and Albert van den Berg, Nano Lett. 11, pp. 2334-2341 (2011).
[17] C. G. Jakobson and Y. Nemirovsky, Electron Devices, IEEE Transactions on, 46, pp. 259-261 (1999).
[18] Xueji Zhang, Huangxian Ju, and Joseph Wang, Electrochemical Sensors, Biosensors and their Biomedical Applications, Academic Press, 2007.

I. Theoretical Frameworks of Giant-Nernst (GN) Scheme

To understand the Giant-Nernst pH response, let us first develop a general model to predict the pH response for decoupled $T_1$-$T_2$ platform and then compare the analytical results with numerical simulations and experimental results. Assume that $T_1$-$T_2$ is the accumulation-type device. Under such linear operating regimes, the drain current modulation in $T_2$ is given as $$\Delta I_{DS,2} = \mu_1 C_{OX,2}(W/L)_2 V_{DS,2} \Delta V_{G,2} \quad (S1)$$

We now consider two operation regimes of GN scheme: If $T_1$ is in accumulation regime, the band bending at the channel surface is very small. Hence the current modulation of $T_1$ due to any pH induced modulation of top-oxide/buffer interface potential ($\Delta V_{G,1}$) is given by, $\Delta I_{DS,1} = \mu_1 C_{OX,1}(W/L)_1 V_{DS,1} \Delta V_{G,1}$. The proposed scheme (FIG. 1c) requires that the bias of $T_2$ should be adjusted to counterbalance the conductance modulation of $T_1$, so that $$\frac{\Delta V_{GS,2}}{\Delta V_{GS,1}} = \left(\frac{\mu_1}{\mu_2}\frac{(W/L)_1}{(W/L)_2}\frac{V_{DS,1}}{V_{DS,2}}\right)\frac{C_{OX,1}}{C_{OX,2}} = \alpha_{GN}\frac{C_{OX,1}}{C_{OX,2}}. \quad (S2)$$

Appropriate design can achieve $\alpha_{GN} \gg 1$ while the maximum amplification of current DGFET schemes is limited by the condition $\alpha_{SN}=1$.

On the other hand, if $T_1$ is in the depletion regime, its conductance modulation is due to the changes in depletion charge. Semi-classical analysis 0 indicates that the depletion charge is given as $Q_1=Q_0(1-\sqrt{1+V_{G,1}/V_0})$ where $Q_0 \equiv \in_{Si} qN_A/C_{OX,1}$ and $V_0 \equiv \in_{Si} qN_A N_A/2C_{OX,1}^2$, respectively. Correspondingly the pH induced current modulation of $T_1$ is equal to $$\Delta I_{DS,1}=\mu_1(W/L)_1 V_{DS,1} Q_0(\sqrt{1+V_{G,1}/V_0}-\sqrt{1+(V_{G,1}+\Delta V_{G,1})/V_0}). \quad (S3)$$

Thus the corresponding sensing signal from $T_2$ can be expressed as $$\Delta V_{G,2} = \alpha_{GN}\frac{Q_0}{C_{OX,2}}\left(\sqrt{1+\frac{V_{G,1}}{V_0}} - \sqrt{1+\frac{V_{G,1}+\Delta V_{G,1}}{V_0}}\right). \quad (S4)$$

Clearly, the pH response is a function of the gate bias in $T_1$ in contrast to the accumulation regime. Equation (S4) can be simplified such that $\Delta V_{G,2} \approx \alpha_{GN} (Q_0/2C_{OX,2}\sqrt{V_0})\Delta V_{G,1}/\sqrt{V_{G,1}}$ if $V_{G,1} \gg \Delta V_{G,1}, V_0$. This analytical expression implies the decrease of sensitivity as the bias ($V_{G,1}$) increases. However, the GN scheme still offers significant amplification over DGFET sensors as $\alpha_{GN} \gg 1$.

Although Eqs. (S2) and (S4) clearly indicate that significant amplification can be achieved through the GN scheme, the above analysis is not complete as the pH dependent modulation of top-oxide/buffer interface potential of $T_1$ ($\Delta V_{G,1}$) is not an independent parameter. Hence, we numerically solve for the electrostatics of the sensor-buffer system, as described by the following equations:

$$-\nabla(\in_w \nabla \Psi) = qn_0(\exp(-\beta\Psi)-\exp(\beta\Psi)), \quad (S5)$$

$$-\nabla(\in_{Si} \nabla \Psi) = q(n_i(\exp(-\beta\Psi)-\exp(\beta\Psi))-N_A), \quad (S6)$$

$$\in_{OX}\nabla\Psi - \in_w\nabla\Psi = \rho_{OH^{2+}} - \rho_{O^-}. \quad (S7)$$

Here $\Psi$ represent the electrostatic potential. Equation (S5) represents the electrostatics of the buffer ($n_0$—ion concentration), while eq. (S6) describes the semiconductor ($n_i$—intrinsic carrier concentration and $N_A$ is the p-type doping density). Eq. (S7) describes top oxide/buffer interface whose RHS denotes the pH dependent charge due to the protonation/de-protonation of surface OH groups. This charge is modeled as function of buffer $H^+$ concentration through the well-known site binding model 0 and will not be discussed in detail here. We self-consistently solve the system of non-linear equations, (S5)-(S7), with appropriate boundary conditions to estimate the charge modulation (and hence the conductance modulation, assuming constant mobility) in the semiconductor due to changes in pH, bias conditions, etc.

Figure 5:
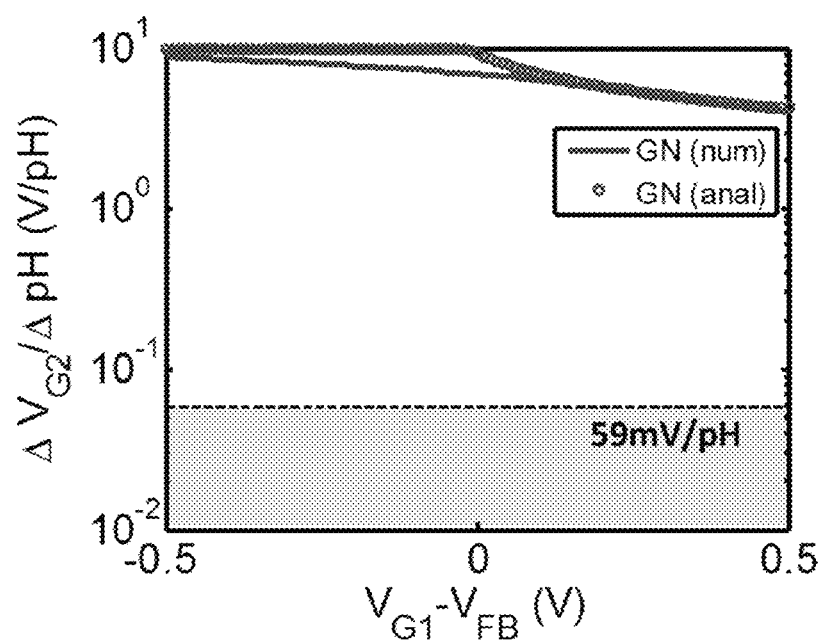
FIG. 5. The theoretical calculation of pH sensitivity using Giant-Nernst scheme. The sensitivity is shown as a function of the bias applied to the fluid gate of the nanoplate ($V_{G,1}$) subtracted by its flat band voltage ($V_{FB}$). Since the analytical simulation is consistent with the numerical simulation, we only use the analytical simulation to interpret the experiment data in the manuscript.

FIG. 5 shows the bias-dependent amplification for GN scheme (symbols indicate numerical simulation results while solid lines indicate analytical results). Here we assume that $T_2$ is in linear regime while the bias applied to $T_1$ is varied. With appropriate design of device geometry, GN scheme achieves ~10V/pH in accumulation regime, which is many orders of magnitude better than the current DGFET sensors (0.1~1V/pH). While in depletion mode of $T_1$ the sensitivity is slightly reduced but still much higher than that of DGFET. In general, therefore one should operate the sensing device in accumulation regime to achieve maximum sensitivity.

II. Noise Consideration of Giant-Nernst (GN) Scheme:
We address the noise and its ratio to the signal (SNR) of our GN scheme, which consists of a nanoplate (NP, $T_1$) and a nanowire (NW, $T_2$). Although there are several sources of noises in ISFET-based pH sensor, we assume that the noise is dominated by the FET's 1/f noise, not by the electrolyte noise ($I_0$~10 mM), which was demonstrated in Ref [3] As we define the sensitivity in terms of the shift in gate voltage ($V_G$) due pH changes, its corresponding noise in $V_G$ ($\sqrt{\langle \delta V_G^2 \rangle}$) dictates SNR.

If the sensor is operated in its linear regime, its noise in terms of the voltage fluctuation is given by the following equations [3]:

$$S_{V_G} = S_{V_{FB}}\left[1 + \left(\alpha\mu_{eff}C_{eff}\frac{I_D}{g_m}\right)\right]^2 \quad (S8)$$

where $$S_{V_{FB}} = \frac{q^2 kTN_t \lambda}{fWLC_{eff}^2}$$

and $$g_m = \frac{dI_D}{dV_G} = \mu_{eff}C_{eff}\frac{W}{L}V_{DS}.$$

Figure 6:
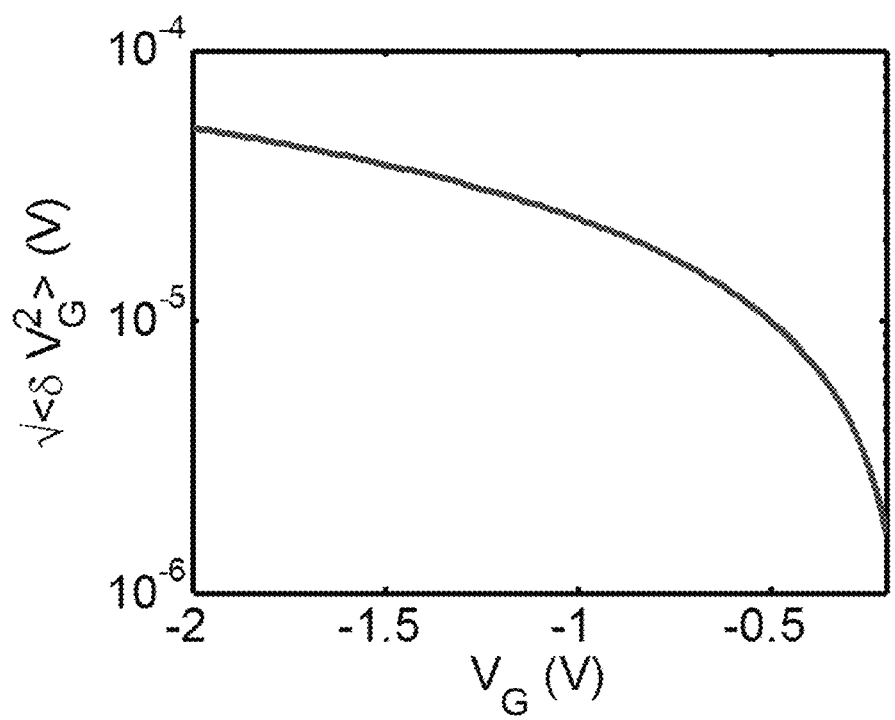
FIG. 6. The calculation of 1/f noise in gate voltage (in log plot). The physical parameters are: W=2 μm, $f_1$=1 Hz, $f_2$=1 kHz, α=1.5×10$^5$ V s/C, λ=0.5 Å, $N_t$=3×10$^{16}$ eV$^{-1}$ cm$^{-3}$, $C_{eff}$=4.73×10$^{-7}$ F/cm$^2$, T=300K.

For a given low ($f_1$) and high frequency cutoff ($f_2$) in the measurement bandwidth, the voltage noise $\sqrt{\langle \delta V_G^2 \rangle}$ is given by $$\sqrt{\langle \delta V_G^2 \rangle} = \sqrt{\frac{q^2 kTN_t \lambda}{WLC_{eff}^2}\ln\left(\frac{f_2}{f_1}\right)}\left[1 + \left(\alpha\mu_{eff}C_{eff}\frac{I_D}{g_m}\right)\right] \quad (S9)$$

where $N_t$ is the volume trap density in the gate oxide layer, $\lambda$ is the tunneling parameter, $C_{eff}$ is the capacitance per area, and a is the coulomb scattering coefficient. Since the noise is given by $\sqrt{\langle \delta V_G^2 \rangle} \sim 1/\sqrt{W}$. And the spectral density of the current is $S_I = g_m^2 S_{V_G}$, therefore the current noise is $\sqrt{\langle \delta I^2 \rangle} = \int_{f_1}^{f_2} S_I(f)df \sim \sqrt{W}$. The calculated voltage noise versus $V_G$ is shown in FIG. 6.

Figure 7:
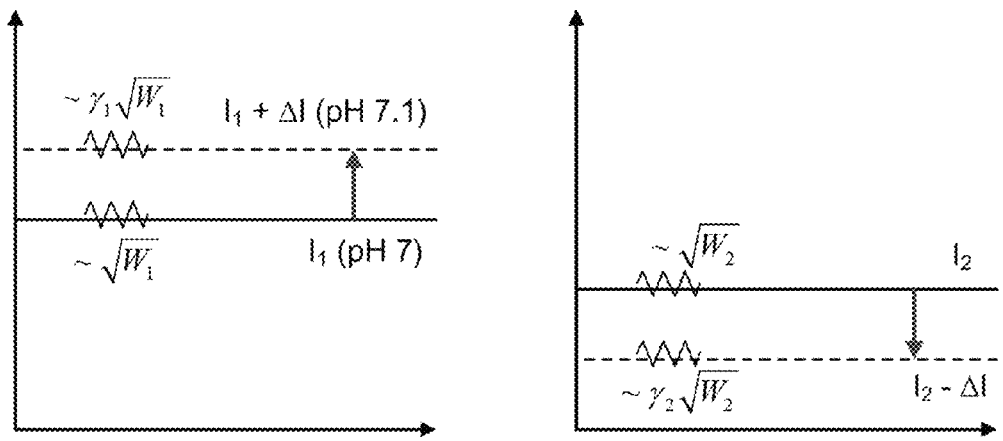
FIG. 7. The conceptual description of current fluctuation in the nanoplate ($T_1$, left) and nanowire ($T_2$, right) due to pH changes (7 to 7.1) and their corresponding current noise. The current change in $T_1$ (ΔI) is compensated by $T_2$.

FIG. 7 shows how the DC current and its noise changes in a nanoplate ($T_1$, left)-nanowire ($T_2$, right) pair. The sum of two DC currents is constant: $I_1+I_2=I$. The initial noise of $T_1$ and $T_2$ is proportional to their widths: $W_1$ and $W_2$, respectively. As the current of T is altered by pH changes its noise magnitude is also changed by a factor of $\gamma$, which is independent of W, where $\gamma$ is defined as $$\gamma_1 = \left[1 + \left(\alpha\mu_{eff}C_{eff}\frac{I_1+\Delta I}{g_m}\right)\right] \Big/ \left[1 + \left(\alpha\mu_{eff}C_{eff}\frac{I_1}{g_m}\right)\right], \quad (S10a)$$

$$\gamma_2 = \left[1 + \left(\alpha\mu_{eff}C_{eff}\frac{I_2-\Delta I}{g_m}\right)\right] \Big/ \left[1 + \left(\alpha\mu_{eff}C_{eff}\frac{I_2}{g_m}\right)\right]. \quad (S10b)$$

The ratio of current and voltage noise between the nanoplate ($T_1$) and nanowire ($T_2$) can be expressed as $$\frac{\sqrt{\langle \delta I_2^2 \rangle}}{\sqrt{\langle \delta I_1^2 \rangle}} = \frac{\gamma_2}{\gamma_1} \frac{\sqrt{W_2}}{\sqrt{W_1}}, \quad (S11)$$

$$\frac{\sqrt{\langle \delta V_{G,2}^2 \rangle}}{\sqrt{\langle \delta V_{G,1}^2 \rangle}} = \frac{\gamma_2}{\gamma_1} \frac{\sqrt{W_1}}{\sqrt{W_2}}.$$

Thus the voltage noise signal is inversely proportional to the square root of width ratio: a nanowire ($T_2$) shows higher noise than that of a nanoplate ($T_1$)

$$\left(\sqrt{\langle \delta V_{G,2} \rangle^2} \gg \sqrt{\langle \delta V_{G,1} \rangle^2}\right)$$

since $W_1 \gg W_2$. This implies that the signal measured at $T_2$ is amplified from signal of $T_1$ by factor of $W_1/W_2$ whereas the corresponding voltage noise ratio is $\sqrt{W_1/W_2}$ (as $\gamma_1/\gamma_2 \approx 1$): Suppose $$W_1/W_2 = 100 \text{ and } \sqrt{\langle \delta V_{G,1} \rangle^2}$$

is 1 mV, then the noise ratio is 10 thus $T_2$ noise is 10 mV, which is the dominant one in the GN scheme ($T_1$-$T_2$). However, even though the noise ratio ($\sqrt{W_1/W_2}$) is smaller the signal amplification factor ($W_1/W_2$), the noise of GN sensor ($T_1$-$T_2$), denoted as $\delta V_{noise}^{NP-NW}$ is fundamentally equal to that of a single nanoplate pH sensor since any signal buried under the noise of NP ($T_1$) in GN scheme ($T_1$-$T_2$) would not be also detectable in $T_2$.

The noise and SNR of pH sensor is directly correlated to the minimum pH resolution, $\Delta pH_{min}$, such that $\Delta pH_{min} = 3 \times \delta V_{noise}/(\Delta V/\Delta pH)$. For any pH sensor we have noise sources from device and measurement instrument as well: for instance, there are two noise sources ($\delta V_{noise}^{NP}$ and $\delta V_{noise}^{Ins}$) in a single nanoplate sensor and its SNR is limited by a larger one between two competitors. Depending on the magnitude of $\delta V_{noise}^{NP}$ and $\delta V_{noise}^{Ins}$ we have two situations for the pH resolution of a single nanoplate sensor:

$$\Delta pH_{min}^{NP} = \begin{cases} 3\delta V_{noise}^{NP}/0.059 & (\text{if } \delta V_{noise}^{Ins} < \delta V_{noise}^{NP}) \\ 3\delta V_{noise}^{Ins}/0.059 & (\text{if } \delta V_{noise}^{Ins} > \delta V_{noise}^{NP}) \end{cases}. \quad (S12)$$

On the other hand, for our GN scheme, we have three noise sources: $\delta V_{noise}^{NP}$, $\delta V_{noise}^{NW}$ and $\delta_{noise}^{Ins}$. Since $\delta V_{noise}^{NW} \gg \delta V_{noise}^{NP}$, in principle there are three different cases depending on the magnitude of the measurement instrument noise $\delta V_{noise}^{Ins}$.

(1) $\delta V_{noise}^{Ins} \leq \delta V_{noise}^{NP} < \delta V_{noise}^{NW}$: Since the signal under the noise ($\delta V_{noise}^{NP}$) in NP ($T_1$) cannot be detected in NW side, the SNR of NP-NW sensor is limited by the NP noise and thus the ideal pH resolution is $\Delta pH_{min}^{NP-NW} \sim 3\delta V_{noise}^{NP}/0.059$ where the pH sensitivity=0.059V/pH.

(2) $\delta V_{noise}^{NP} < \delta V_{noise}^{Ins} < \delta V_{noise}^{NW}$: First in a NP-alone sensor, its pH resolution is clearly equal to $3\delta V_{noise}^{Ins}/0.059$. In a NP-NW sensor, the pH resolution of NP ($T_1$) itself is $\Delta pH_{min}^{NP} \sim 3\delta V_{noise}^{NP}/0.059$. On the other hand, NP-NW pair-wise, a voltage signal (from NP) larger than $\delta V_{noise}^{NP}$ can be amplified by the factor $\alpha_{GN}$ (where $\alpha_{GN} = W_1/W_2 \gg 1$), thus the additional competing factor is $\Delta pH_{min}^{NW} \sim 3\delta V_{noise}^{NW}/(0.059 \times \alpha_{GN})$. The ratio of pH resolution between two competing factors is given by $\Delta pH_{min}^{NP}/\Delta pH_{min}^{NW} \sim \alpha_{GN}(\delta V_{noise}^{NP}/\delta V_{noise}^{NW})$. Since $(\delta V_{noise}^{NP}/\delta V_{noise}^{NW}) \sim 1/\sqrt{W_1/W_2}$, $\Delta pH_{min}^{NP}/\Delta pH_{min}^{NW} \approx \sqrt{W_1/W_2} > 1$. Since the overall pH resolution is limited by larger (i.e., worse) one among two competing factors, where $\Delta pH_{min}^{NP} > \Delta pH_{min}^{NW}$ in this case, $\Delta pH_{min}^{NP-NW} = \Delta pH_{min}^{NP} \sim 3\delta V_{noise}^{NP}/0.059$.

(3) $\delta V_{noise}^{NP} < \delta V_{noise}^{NW} < \delta V_{noise}^{Ins}$: This case is similar to Case (2), but here the competing resolution in NW side is $\Delta pH_{min}^{NW} \sim 3\delta V_{noise}^{Ins}/(0.059 \times \alpha_{GN})$ since now $\delta V_{noise}^{Ins} > \delta V_{noise}^{NW}$. Again, the ratio of pH resolution between two competing factors is given by $\Delta pH_{min}^{NP}/\Delta pH_{min}^{NW} \sim \alpha_{GN}(\delta V_{noise}^{NP}/\delta V_{noise}^{Ins})$. Since $\delta V_{noise}^{NW} < \delta V_{noise}^{Ins}$, $\Delta pH_{min}^{NP}/\Delta pH_{min}^{NW} \sim \alpha_{GN} (\delta V_{noise}^{NP}/\delta V_{noise}^{Ins}) = \sqrt{\alpha_{GN}}(\delta V_{noise}^{NW}/\delta V_{noise}^{Ins})$. Depending on the magnitude of $\delta V_{noise}^{Ins}$ we have two different answers:

$$\Delta pH_{min}^{NP}/\Delta pH_{min}^{NW} \begin{cases} > 1 & (\text{if } \delta V_{noise}^{Ins} < \sqrt{\alpha_{GN}} \delta V_{noise}^{NW} = \alpha_{GN} \delta V_{noise}^{NP}) \\ < 1 & (\text{if } \delta V_{noise}^{Ins} > \sqrt{\alpha_{GN}} \delta V_{noise}^{NW} = \alpha_{GN} \delta V_{noise}^{NP}) \end{cases}. \quad (S13)$$

The corresponding overall pH resolution has also two different answers:

$$\Delta pH_{min}^{NP-NW} = \max(\Delta pH_{min}^{NP}, \Delta pH_{min}^{NW}) = \quad (S14)$$

$$\begin{cases} \dfrac{3\delta V_{noise}^{NP}}{0.059} & (\text{if } \delta V_{noise}^{Ins} < \sqrt{\alpha_{GN}} \delta V_{noise}^{NW} = \alpha_{GN} \delta V_{noise}^{NP}) \\ \dfrac{3\delta V_{noise}^{Ins}}{0.059 \times \alpha_{GN}} & (\text{if } \delta V_{noise}^{Ins} > \sqrt{\alpha_{GN}} \delta V_{noise}^{NW} = \alpha_{GN} \delta V_{noise}^{NP}) \end{cases}.$$

If we compare the ratio of $\Delta pH_{min}^{NP-NW}$ and $\Delta pH_{min}^{NP}$, $$\frac{\Delta pH_{min}^{NP-NW}}{\Delta pH_{min}^{NP}} = \quad (S15)$$

$$\begin{cases} \delta V_{noise}^{NP}/\delta V_{noise}^{Ins} & (\text{if } \delta V_{noise}^{Ins} < \sqrt{\alpha_{GN}} \delta V_{noise}^{NW} = \alpha_{GN} \delta V_{noise}^{NP}) \\ 1/\alpha_{GN} & (\text{if } \delta V_{noise}^{Ins} > \sqrt{\alpha_{GN}} \delta V_{noise}^{NW} = \alpha_{GN} \delta V_{noise}^{NP}) \end{cases}.$$

For the first case of eq. (S15) $\sqrt{\alpha_{GN}} \delta V_{noise}^{NP} < \delta V_{noise}^{Ins} < \alpha_{GN} \delta V_{noise}^{NP}$, thus $$\frac{1}{\alpha_{GN}} < \frac{\delta V_{noise}^{NP}}{\delta V_{noise}^{Ins}} < \frac{1}{\sqrt{\alpha_{GN}}} < 1.$$

So, in the Case (3), regardless of the magnitude of $\delta V_{noise}^{Ins}$ we always achieve smaller (i.e., better) pH resolution in GN (NP-NW) scheme compared to a single NP sensor.

We summarize pH resolution of a single NP sensor ($\Delta pH_{min}^{NP}$) and GN scheme ($\Delta pH_{min}^{NP-NW}$) for the three possible cases in the following table:

TABLE S1

The comparison of pH resolution for NP sensor alone and proposed GN scheme.

| | NP alone ($T_1$) | GN scheme ($T_1$-$T_2$) | Comparison of $\Delta pH_{min}$ |
|---|---|---|---|
| $\delta V_{noise}^{Ins} <$ $\delta V_{noise}^{NP} <$ $\delta V_{noise}^{NW}$ | $3\delta V_{noise}^{NP}/0.059$ | $3\delta V_{noise}^{NP}/0.059$ | $\Delta pH_{min}^{NP} =$ $\Delta pH_{min}^{NP-NW}$ |
| $\delta V_{noise}^{NP} <$ $\delta V_{noise}^{Ins} <$ $\delta V_{noise}^{NW}$ | $3\delta V_{noise}^{Ins}/0.059$ | $3\delta V_{noise}^{NP}/0.059$ | $\Delta pH_{min}^{NP} >$ $\Delta pH_{min}^{NP-NW}$ |
| $\delta V_{noise}^{NP} <$ $\delta V_{noise}^{NW} <$ $\delta V_{noise}^{Ins}$ | $3\delta V_{noise}^{Ins}/0.059$ | $3\delta V_{noise}^{NP}/(0.059 \times \alpha_{GN})$ or $3\delta V_{noise}^{NP}/0.059$ | $\Delta pH_{min}^{NP} >>$ $\Delta pH_{min}^{NP-NW}$ |

Among all the three possible cases, GN scheme has its advantage over NP-alone sensor in terms of pH resolution in Cases (2) and (3) in which the pH resolution of GN scheme is much smaller than that of a single NP sensor. Since Cases (2) and (3) are the dominant situation especially for the point-of-care devices whose measurement instrument is not sophisticated enough ($\delta V_{noise}^{NP} \sim 1\text{-}10$ µV in general), the GN scheme always enhance the minimum pH resolution by the factor of $\alpha_{GN}$ for the sensors with relatively low-precision instruments.

Figure 8:
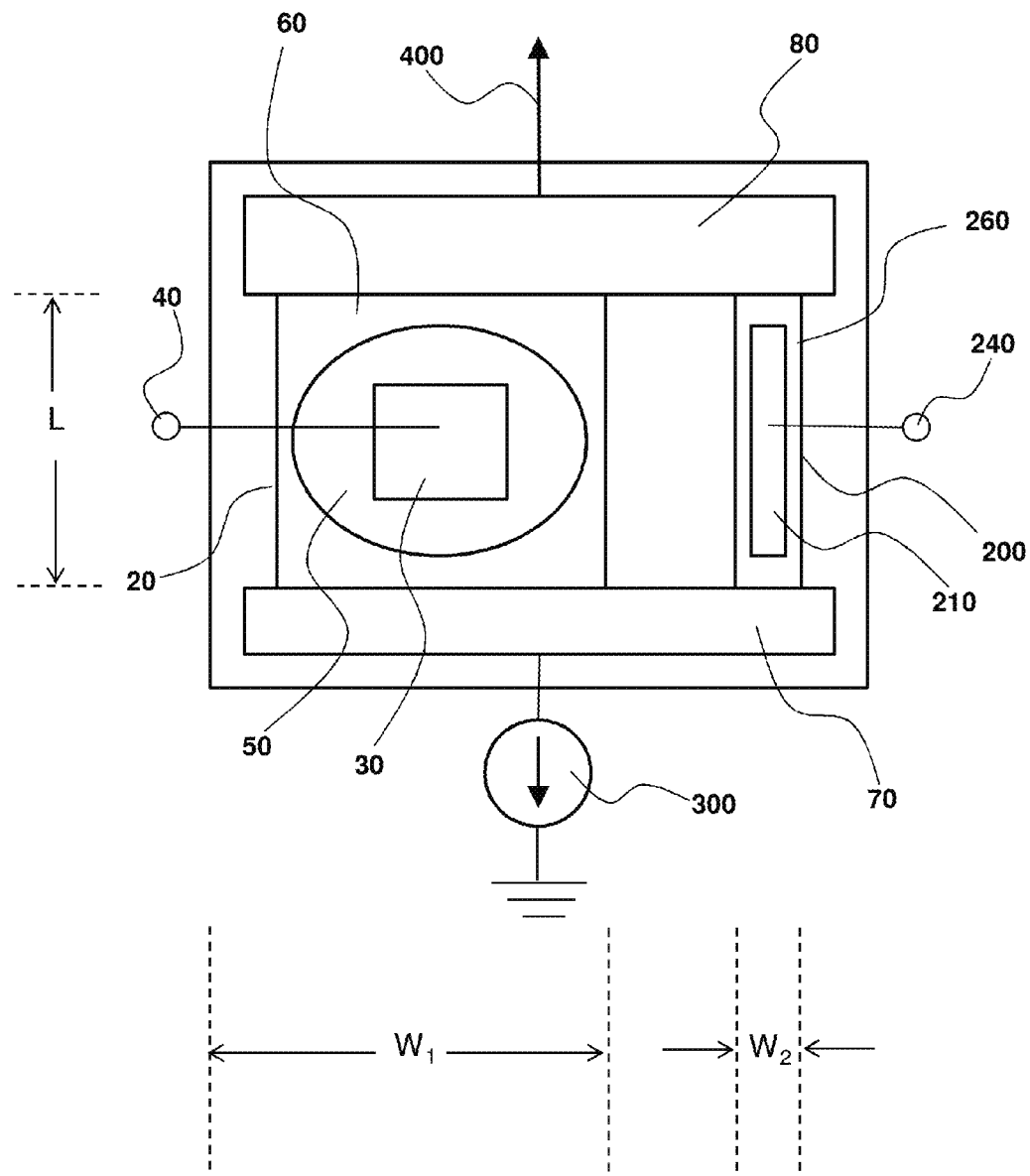
FIG. 8. Schematic of a device for amplifying a pH signal and measuring pH.

An example of one embodiment of a device 10 for measuring pH, including monitoring a change in pH over time, is schematically illustrated in FIGS. 1(c), 1(d) and FIG. 8. The device has a sensor 20 and a transducer 200. The sensor 20 comprises a fluid gate 30 and corresponding fluid gate bias 40 ($V_{G,1}$). The fluid gate 30 is at least partially immersed in a material or fluid 50 in which pH is measured. A sensor channel 60 is positioned between a source electrode 70 and a drain electrode 80 along with a sensing surface 65 that physically contacts and supports the fluid 50. The sensor channel may further comprise a layer 62 that interacts with the fluid to generate a detectable electrical property, such as transconductance that is modulated based on the pH of the fluid. The layer 62 may be an oxide layer, as illustrated in FIG. 1(a). In an embodiment, the sensor channel 60 is a nanoplate (labeled NP in FIG. 1(d)).

The transducer 200 comprises a top or bottom gate 210 (see FIG. 1(d) top panel for bottom gate embodiment and bottom panel for top gate embodiment) and corresponding gate bias 240 ($V_{G,2}$). In this embodiment, source and drain electrodes are illustrated as corresponding to the source 70 and drain 80 electrodes of the sensor. Optionally, source and drain electrodes used with the transducer 200, are separate and distinct from those used with the sensor 20. A transducer channel 260 is positioned between the source and drain electrodes. The illustrated embodiment depicts fluid droplet 50 that is not in contact with the transducer 200. Optionally, the sensor and transducer channels from a fluid well for receiving a fluid 50, in which case the transducer is configured such that the transconductance of the transducer is substantially independent or is independent of pH changes in the fluid and the transducer may have a transducer surface in contact with the fluid. "Substantially independent" refers to a transconductance that varies less than 10%, less than 5%, less than 1%, or less than 0.1%, with a selected change in pH. Referring to FIGS. 1(c), (d), and 8, the transducer channel may be nanowire (NW). The sensor and transducer channel widths are $W_1$ and $W_2$, respectively. Similarly, $L_1$ and $L_2$ defines the sensor and transducer channel lengths. The illustrated embodiment shows those lengths as equal and corresponding to the distance between the source and drain. Optionally, the lengths are not equal. Optionally, any of the lengths may be less than the separation distance between the source and drain, such as by patterning of sensor, transducer, source or drain shape, including by one or more channel ends that are separated from source and drain, but electrically connected thereto by an electrical interconnection. In use, a channel current 300 ($I_D$), including a source-drain current for each of the sensor ($I_{D,1}$) and transducer ($I_{D,2}$) is monitored along with drain bias 400 ($V_{DD}$), including the drain bias of the sensor ($V_{D,1}$) and the transducer ($V_{D,2}$), thereby measuring pH, including detecting changes in pH, by the amplification factor arising from the unique sensor and transducer configurations.

References

[1] Y. Taur and T. H. Ning, *Fundamentals of Modern VLSI Devices*, Cambridge University Press, Cambridge, UK, 1998.
[2] S. L. David E. Yates and T. W. Healy, "Site-binding model of the electrical double layer at the oxide/water interface," *Journal of the Chemical Society, Faraday Transactions 1: Physical Chemistry in Condensed Phases*, vol. 70, pp. 1807-1818, 1974.
[3] M. J. Deen, M. W. Shinwari, J. C. Ranuárez, and D. Landheer, "Noise considerations in field-effect biosensors," *Journal of Applied Physics*, vol. 100, p. 074703 (2006).

Example 3

Ultrasensitive pH Detection by Nanowire-Nanoplate Combination Sensor

Figure 9:
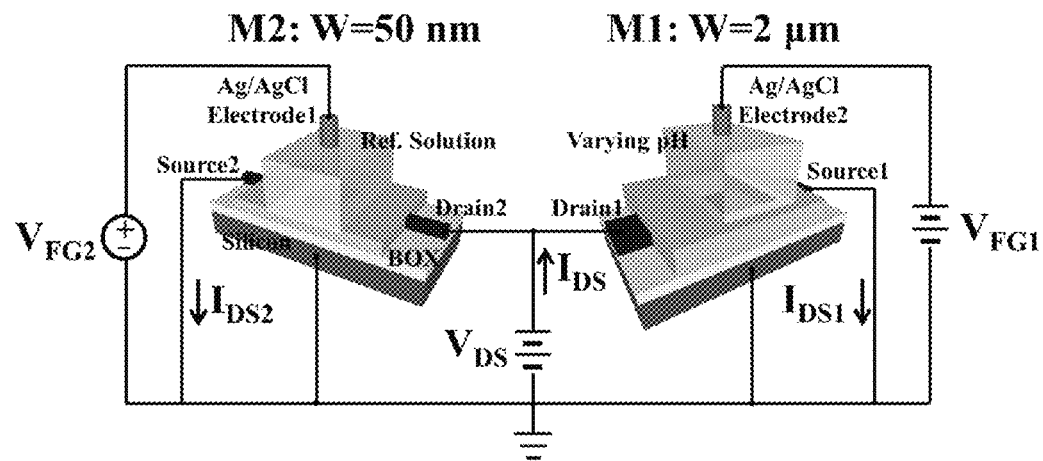
FIG. 9. Schematic of a nanowire-nanoplate pH sensor configuration. A constant DC bias is applied to the gate of T2, the plate device. The gate of T1, the wire, is swept while the total current I is measured as a function of the pH over T2.

A schematic demonstrating the nanowire-nanoplate combination sensor is shown in FIG. 9. Two devices of varying width are biased in parallel. T1 is a nanoplate device with width of 2 µm, and T2 is a nanowire device with width of 50 nm. The output current is measured at the shorted drain nodes of the devices as indicated. This current is the sum of the source-drain current for both devices: $I = I_{DS1} + I_{DS2}$.

Figure 11:
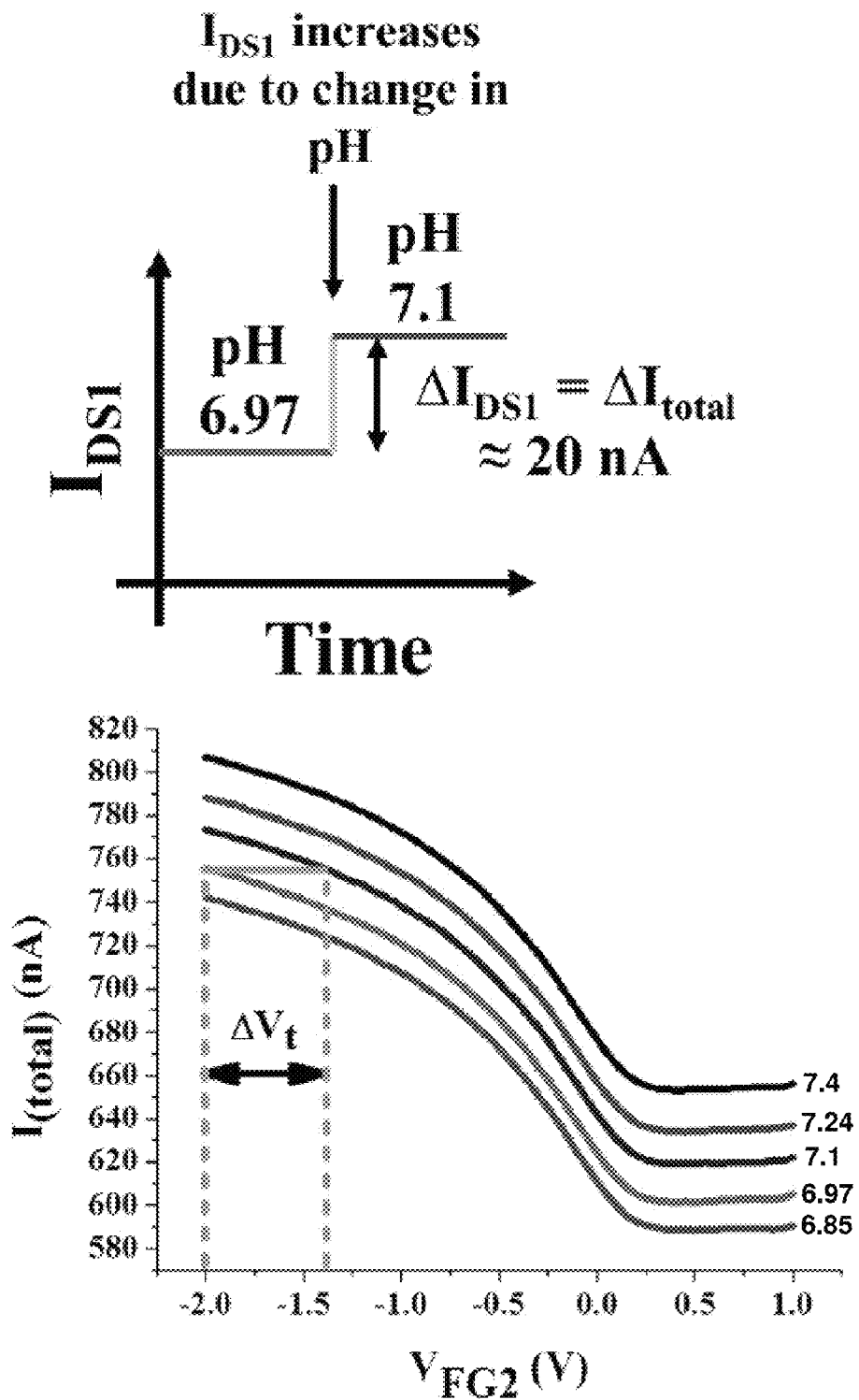
FIG. 11. The transfer characteristics of the combined nanowire-nanoplate device as a function of pH. The line associated with $\Delta V_t$ shows an example of how the shift in threshold voltage for the device is calculated.

The two transistors have separate fluid wells and separate reference electrodes, which can be used to control the separate fluid potentials separately. T1 is considered to be the sensing element, and is exposed to solutions of varying pH with a fixed gate bias, $V_{FG2}$. T2 is the "transducer" element, and is exposed to only a reference solution throughout the experiments. Transfer characteristics of T2 are used as the output characteristic (by sweeping $V_{FG1}$), while the pH of the solutions over T2 is the input characteristic. As the pH is changed over T1, large changes in the total current I will be induced due to the surface potential changes over T1. In order to counterbalance these large changes in current to preserve the same total current I, very large shifts in the I-$V_{FG2}$ are required, as illustrated in FIG. 11. These large shifts are amplified by a factor of approximately W2/W1 (about 40 in this case). This leads to a dramatic decrease in the smallest pH shift that is detectable by the system.

Figure 10:
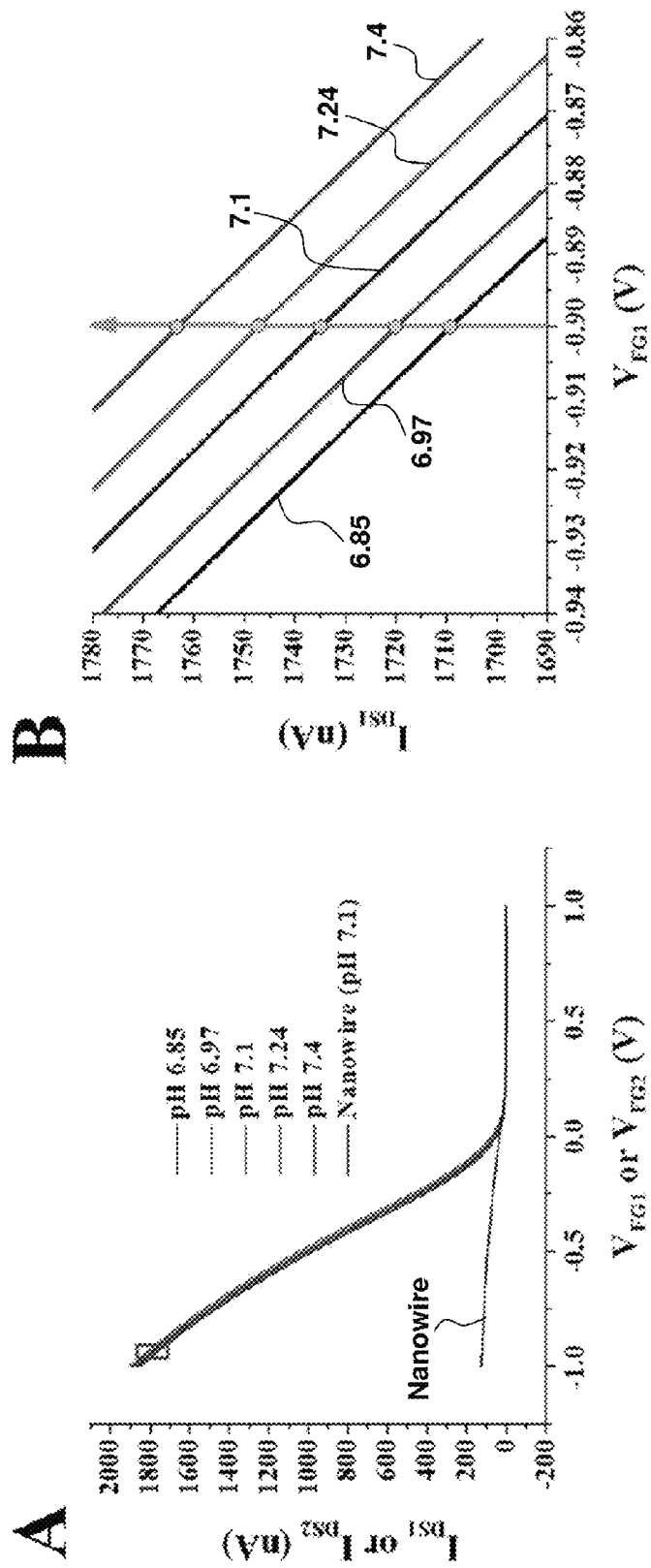
FIG. 10. A—Transfer characteristics for the nanoplate (for 5 different pH values) and for the nanowire. B—Zoomed in region around the rectangle in part A.

Individual transfer characteristics of the nanowire device and the nanoplate device at five different pH values are shown in FIG. 10. The nanowire current is seen to be significantly lower ($\approx 20\times$) than the current through the plate. A blown up view of the nanoplate as a function of changing pH is shown in FIG. 10B. Values around physiological pH are selected for higher relevance, and pH points are designed very close to one another, since this scheme lends itself well for very high sensitivity but low dynamic range measurements. The current through T1, the nanoplate in the pH solutions, $I_{DS1}$, can be seen to monotonically increase with increasing pH, at about 12-13 nA per 0.1 pH increase. We highlight the vertical line at $V_{FG1}=-0.9V$, since this is the low constant bias applied to T1 to keep it in accumulation during the experiments.

The two devices are then connected as shown in FIG. 9, and exposed to the different pH solutions. Transfer characteristics are extracted by sweeping $V_{FG1}$ and measuring the total current $I_{total}$. Results are shown in FIG. 11. The method for determining the shift in "threshold voltage" is also demonstrated, where essentially we take a constant current, and determine where each curve intersects a horizontal line through this current. Five sweeps are taken per pH point to quantify the average noise of the nanoplate (3.45 mV), the nanowire (2.63 mV), and of the combined system. Results for each shift, including the noise of the combined system are shown in Table 2. Volts per pH is the sensitivity factor previously discussed, given by:

$$S = \frac{\Delta V_t}{\Delta pH} \quad (1)$$

This sensitivity factor is approximately equal to:

$$S = \alpha(0.059 \text{ V/pH}) \quad (2)$$

Using this sensitivity factor and the extracted noise for each point, we can calculate the minimum detectable pH resolution, given by:

$$\Delta pH_{min} = \frac{3}{\alpha/\delta V_t} \quad (3)$$

Figure 12:
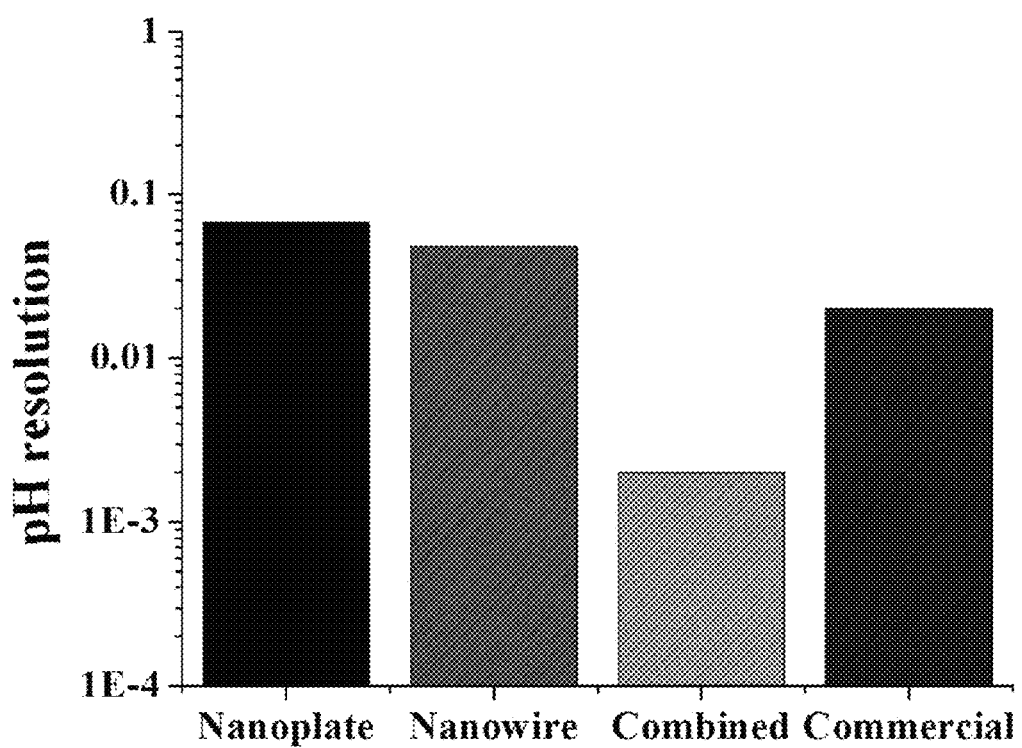
FIG. 12. Comparison of the minimum pH detection resolution to commercial sensors, to an individual nanoplate, and to an individual nanowire sensor.

These values are plotted in Table 2. For the four shifts noted, the highest $\Delta pH_{min}$ observed is less than 0.002 pH units, around an order of magnitude better than any pH sensor currently available. A comparison of this minimum pH resolution to individual nanoplate, nanowire, and commercial devices is shown in FIG. 12. This technique has very small dynamic range, which is limited by the window in which the transfer characteristics are swept (for example, from +1 to -2 V in FIG. 11). It is intended as a very sensitive measurements of pH values that will not change significantly over time—for example, for use as intracellular or extracellular pH detectors in tumor cell environments.

TABLE 2

Summary of sensitivity and achievable minimum pH resolutions.

| pH Shift | Sensitivity: S (V/pH) | Noise: $\delta V_t$ (mV) | Signal to Noise Ratio | pH Resolution $pH_{min}$ |
|---|---|---|---|---|
| 6.85 to 6.97 | 4.24 | 2.36 | 1798 | 0.00167 |
| 6.97 to 7.1 | 4.51 | 1.28 | 3525 | 0.00085 |
| 7.1 to 7.24 | 3.72 | 2.01 | 1848 | 0.00162 |
| 7.24 to 7.4 | 3.94 | 1.10 | 3582 | 0.00084 |

In conclusion, we demonstrate the use of a nanowire-nanoplate combination sensor for the detection of pH units down to 0.002, which is an order of magnitude better than commercial sensors and is, to our knowledge, the most sensitive bioFET pH sensor reported to date. An increase in the observed signal is achieved by a huge difference in the source-drain currents of the two devices, which is used to induce a large threshold shift for the nanowire device due to pH changes on the nanoplate device. The measured noise is not enhanced in this process due to an environmental noise factor that is larger than the intrinsic nanoplate and nanowire noise. As long as the intrinsic nanoplate noise is kept to lower than the environmental noise divided by $\alpha$, the amplification factor, the resulting pH sensitivity will be $\alpha(0.059 \text{ mV/pH})$. This method for ultrasensitive detection can be used for many applications.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference). Various patent documents are specifically referred to for the various electronic devices and processes related thereto, including FETs and related components for use in various applications, including: US 20110086352; WO 2012/078340; US 20080280776; WO 2010/037085; WO 2011/163058; WO 2013/016486.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure. Specific names of compounds are intended to be exemplary, as it is known that one of ordinary skill in the art can name the same compounds differently. Every formulation or combination of components described or exemplified herein can be used to practice the invention, unless otherwise stated.

Whenever a range is given in the specification, for example, a ratio range, a size range, a pH range, a sensitivity range, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method of amplifying a pH signal, the method comprising the steps of:
    providing a sensor comprising a source electrode, a drain electrode, a sensor channel provided between the source and drain electrodes, and a sensing surface over at least a portion of the sensor channel, wherein the sensor channel has a first transconductance;
    providing a transducer comprising a source electrode, a drain electrode, and a transducer channel provided between the source and drain electrodes, wherein the transducer channel has a second transconductance, and the second transconductance is greater than the first transconductance;
    applying a material to the sensing surface, wherein a change in pH generates a conductance modulation of the sensor channel; and
    adjusting a bias of the transducer to counterbalance the conductance modulation of the sensor channel; thereby amplifying the pH signal of the material;
    wherein the amplifying corresponds to an amplification factor defined by:

$$\left( \frac{\mu_1}{\mu_2} \frac{(W/L)_1}{(W/L)_2} \frac{V_{DS,1}}{V_{DS,2}} \right) \frac{C_{OX,1}}{C_{OX,2}}$$

wherein $\mu$ is the channel mobility, W is the channel width, L is the channel length, $V_{DS}$ is the drain bias, $C_{OX}$ is the gate oxide capacitance, and the subscripts 1 and 2 refer to the sensor and the transducer, respectively;
    the method further comprising the step of selecting an amplification factor that is greater than or equal to 10.

2. The method of claim 1, wherein the amplification factor is greater than or equal to 20.

3. The method of claim 2, wherein the selecting step comprises selecting a width and/or a length of: the transducer channel, the sensor channel, or both, so that $(W/L)_1/(W/L)_2$ is greater than or equal to 20.

4. The method of claim 3, wherein the sensor channel is a nanoplate and the transducer channel is a nanowire.

5. The method of claim 2, wherein the selecting step comprises mobility scaling so that the sensor channel has a higher mobility than a transducer channel mobility, and wherein the mobility scaling comprises:
    providing a first material for the sensor channel and a second material for the transducer channel, wherein the first material has a higher mobility than the second material; or
    providing the sensor as part of an n-channel metal-oxide-semiconductor field-effect transistor (nMOS) and the transducer as part of a p-channel metal-oxide-semiconductor field-effect transistor (pMOS).

6. The method of claim 2, wherein the selecting step comprises oxide thickness scaling so that $C_{OX,1}$ is greater than $C_{OX,2}$ by at least a factor of 20.

7. The method of claim 6, wherein the oxide thickness scaling comprises:
    a dual oxide process to provide an oxide layer thickness of the sensor that is greater than an oxide layer thickness of the transducer; or
    providing a sensor channel material having a higher k-dielectric than a transducer channel material k-dielectric; or
    providing an oxide layer thickness of the sensor that is greater than an oxide layer thickness of the transducer by a dual oxide process and providing a sensor channel material that is a higher k-dielectric than the transducer channel material.

8. The method of claim 2, wherein the selecting step comprises bias scaling so that $V_{DS,1}$ is greater than or equal to $V_{DS,2}$ by a factor of at least 20; and wherein the bias scaling provides real-time tunability of sensor performance.

9. The method of claim 1, wherein:
    the transducer channel is biased to a top gate or to a bottom gate; or
    the sensor channel is biased to a fluid gate that is at least partially immersed in the material.

10. The method of claim 1, wherein the transducer further comprises a transducer surface and the material is provided on the transducer surface, wherein the second transconductance is substantially independent of pH.

11. The method of claim 1, wherein the transducer is positioned outside of a well in which the material is confined.

12. The method of claim 1, used in an application selected from the group consisting of nucleotide sequencing, environmental toxic monitoring, pharmaceutical testing, food testing, cancer monitoring, and detection of enzyme activity.

13. The method of claim 1, wherein the material comprises a fluid electrolyte.

14. The method of claim 1, wherein the material comprises a biological cell and intracellular pH is measured, extracellular pH is measured, or both intracellular and extracellular pH is measured.

15. The method of claim 1, wherein the sensing surface comprises an oxide surface and wherein:
   the oxide surface interacts with a proton; or
   the oxide surface comprises OH surface groups that react with protons to provide a sensor channel transconductance modulation that is pH dependent.

* * * * *